(12) United States Patent
Russell et al.

(10) Patent No.: US 7,524,494 B2
(45) Date of Patent: Apr. 28, 2009

(54) DEGRADATION OF HYDROPHOBIC ESTER PESTICIDES AND TOXINS

(75) Inventors: Robyn Joyce Russell, Wanniassa (AU); Rama Heidari, Amaroo (AU); Alan Devonshire, Harpenden (GB); Susan Jane Dorrian, Fraser (AU); John Graham Oakeshott, Wanniassa (AU)

(73) Assignee: Commonwealth Scientific and Industrial Research Organisation (AU)

( * ) Notice: Subject to any disclaimer, the term of this patent is extended or adjusted under 35 U.S.C. 154(b) by 351 days.

(21) Appl. No.: 10/503,643

(22) PCT Filed: Feb. 6, 2002

(86) PCT No.: PCT/AU02/00114

§ 371 (c)(1),
(2), (4) Date: Mar. 23, 2005

(87) PCT Pub. No.: WO03/066874

PCT Pub. Date: Aug. 14, 2003

(65) Prior Publication Data

US 2005/0176117 A1  Aug. 11, 2005

(51) Int. Cl.
*A61K 38/46* (2006.01)
*C12N 9/18* (2006.01)
*C12N 1/20* (2006.01)
*C12N 15/00* (2006.01)
*C07H 21/04* (2006.01)

(52) U.S. Cl. ............... 424/94.6; 435/197; 435/252.3; 435/320.1; 536/23.2

(58) Field of Classification Search ............... 435/197, 435/252.3, 320.1; 424/94.6; 536/23.2
See application file for complete search history.

(56) References Cited

U.S. PATENT DOCUMENTS

| | | | |
|---|---|---|---|
| 4,945,050 A | 7/1990 | Sanford et al. | |
| 5,004,863 A | 4/1991 | Umbeck | |
| 5,104,310 A | 4/1992 | Saltin | |
| 5,141,131 A | 8/1992 | Miller, Jr. et al. | |
| 5,159,135 A | 10/1992 | Umbeck | |
| 5,177,010 A | 1/1993 | Goldman et al. | |
| 5,384,253 A | 1/1995 | Krzyzek et al. | |
| 5,472,869 A | 12/1995 | Krzyzek et al. | |
| 5,516,674 A | 5/1996 | Roe et al. | |
| 5,843,758 A * | 12/1998 | Russell et al. | ............ 435/252.3 |
| 7,091,025 B2 * | 8/2006 | Russell et al. | ............... 435/197 |

FOREIGN PATENT DOCUMENTS

| | | |
|---|---|---|
| WO | WO 92/09696 | 6/1992 |
| WO | WO 93/21335 | 10/1993 |
| WO | 9519440 | 7/1995 |
| WO | WO 00/64539 | 11/2000 |

OTHER PUBLICATIONS

Bisset et al. (1997) "Cross-Resistance to Pyrethroid and Organophosphorus Insecticides in the Southern House Mosquito (Diptera: Culicidae) from Cuba," *J. Med. Entomol.* 34(2):244-246.
Heidari et al. (Jun. 2005) "Hydrolysis of Pyrethroids by Carboxylesterases from *Lucilia cuprina* and *Drosophila melanogaster* with Active Sites Modified by in Vitro Mutagenesis," *Insect Biochem. Mol. Biol.* 35:597-609.
Hernandez et al. (Oct. 2000) "Identification of a Point Mutation in an Esterase Gene in Different Populations of the Southern Cattle Tick, Boophilus microplus," *Insect Biochem. Mol. Biol.* 30:969-977.
Newcomb et al. (1996) "*Lucilia cuprina* LCAE7 Gene, E3," EBI Accession No. Q25252.
Robin et al. (1996) "*Drosophila melanogaster* ALPHA-EST7 Gene, Alpha Esterase," EBI Accession No. Q24201.
Billecke et al. (1999) "Characterization of a Soluble Mouse Liver Enzyme Capable of Hydrolyzing Diisopropyl Phosphorofluridate," *Chemico-Biological Interactions* 120:251-256.
Campbell et al. (Apr. 2001) "Identification of a Juvenile Hormone Esterase Gene by Matching its Peptide Mass Fingerprint with a Sequence from the Drosophila Genome Project," *Insect Biochem. Mol. Biol.* 31:513-520.
Campbell et al. (1998) "Two Different Amino Acid Substitutions in the Ali-esterase, E3, Confer Alternative Types of Organophosphorus Insecticide Resistance in the Sheep Blowfly, *Lucilia cuprina*," *Insect Biochem. Mol. Biol.* 28:139-150.
Campbell et al. (1998) "Cross-Resistance Patterns Among *Lucilia cuprina* (Diptera:Calliphoridae) Resistant to Organophosphorus Insecticides," *J. Econ. Entomol.* 91:367-375.
Claudianos et al. (1999) "The Same Amino Acid Substitution in Orthologous Esterases Confers Organophosphate Resistance on the House Fly and Blowfly," *Insect Biochem. Mol. Biol.* 29:675-686.
Claudianos et al. (2002) "A Genomics Perspective on Mutant Aliesterases and Metabolic Resistance to Organophosphates," In:*Agrochemical Resistance: Extent, Mechanism and Detection*, Marshall Clark, J. and Yamagushi, I. (Eds) 90-101.
Cygler et al. (1997) "Structure as Basis for Understanding Interfacial Properties of Lipases," *Methods Enzymol.* 284:3-27.
Derewenda et al. (1992) "Catalysis at the Interface: The Anatomy of a Conformational Change in a Triglyceride Lipase," *Biochem.* 31:1532-1541.
Devonshire et al. (1982) "A Carboxylesterase with Broad Substrate Specificity Causes Organophosphorus, Carbamate and Pyrethroid Resistance in Peach—Potato Aphids (*Myzus persicae*)," *Pestic. Biochem. Physiol.* 18:235-246.
Devonshire et al. (2003) "Kinetic Efficiency of Mutant Carboxylesterases Implicated in Organophosphate Insecticide Resistance," *Pest. Biochem. Physiol.* 76:1-13.

(Continued)

*Primary Examiner*—Tekchand Saidha
(74) *Attorney, Agent, or Firm*—Greenlee, Winner and Sullivan, P.C.

(57) ABSTRACT

The present invention relates to methods and enzymes for degrading hydrophobic ester pesticides and toxins. In particular, the present invention relates to the use of insect esterases, and mutants thereof, in the bioremediation of hydrophobic ester pesticides and toxins residues, such as pyrethroid residues, contaminating the environment and horticultural commodities.

26 Claims, 5 Drawing Sheets

OTHER PUBLICATIONS

Figure 2:
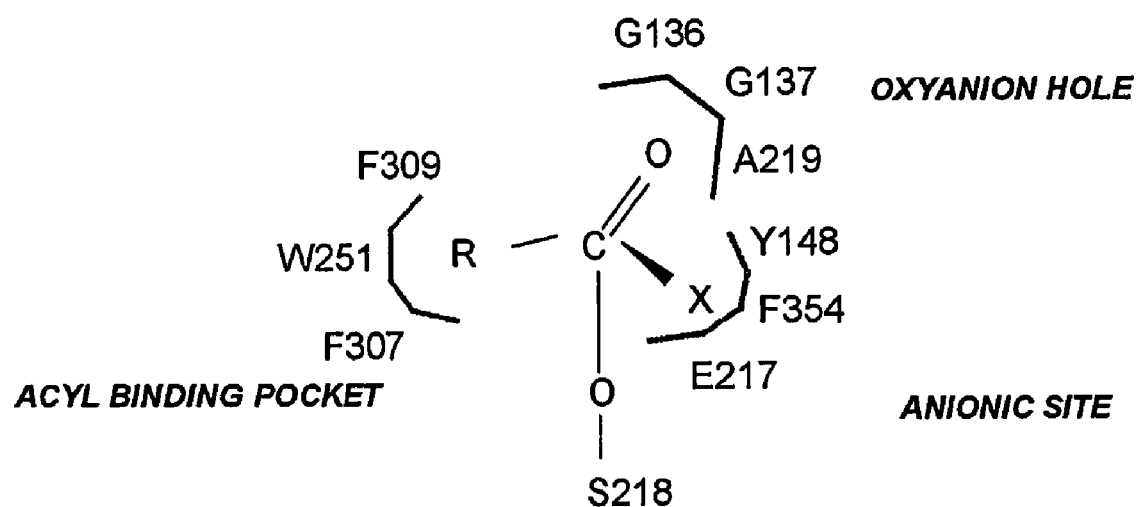

Field et al. (1993) "Cloning and Analysis of the Esterase Genes Conferring Insecticide resistance in the Peach-Potato Aphid, *Myzus persicae* (Sulzer)," *Biochem. J.* 294:569-574.

Fournier et al. (1992) "Acetylcholinesterase," *J. Biol. Chem.* 267:14270-14274.

Gordon et al. (1999) "Organophosphate Skin Decontamination Using Immobilized Enzymes," *Chem. Biol. Interact.* 119-120:463-470.

Grochulski et al. (1993) "Insights into Interfacial Activation from an Open Structure of *Candida rugosa* Lipase," *J. Biol. Chem.* 268:12843-12847.

Harel et al. (2000) "Three-Dimensional Structures of *Drosophila melanogaster* Acetylcholinesterase and of its Complexes with Two Potent Inhibitors," *Protein Sci.* 9:1063-1072.

Jarv, J. (1984) "Stereochemical Aspects of Cholinesterase Catalysis," *Bioorganic Chemistry* 12:259-278.

Koellner et al. (2000) "Active-Site Gorge and Buries Water Molecules in Crystal Structures of Acetylcholinesterase from *Torpedo californica*," *J. Mol. Biol.* 296:713-735.

Lee et al. (Jun. 2001) "Biochemical Mechanisms of Resistance in Strains of *Oryzaephilus surinamensis* (Coleoptera: Silvanidae) Resistant to Malathion and Chlorpyrifos-Methyl," *J. Econ. Entomol.* 94(3):706-713.

LeJeune et al. (1998) "Nerve Agents Degraded by Enzymatic Foams," *Nature* 395:27-28.

Martinez et al. (1994) "Cutinase, a Lipolytic Enzyme with a Preformed Oxyanion Hole," *Biochem.* 33:83-89.

Meyers et al. (1993) "Effects of the Residue Adjacent to the Reactive Serine on the Substrate Interactions of *Drosophila* Esterase 6," *Biochem. Genet.* 31:259-278.

Nair et al. (1994) "Molecular Recognition in Acetylcholinesterase Catalysis: Free-Energy Correlations for Substrate Turnover and Inhibition by Trifluoro Ketone Transition-State Analogs," *Biochem.* 33:8566-8576.

Newcomb et al. (1997) "A Single Amino Acid Substitution Converts a Carboxylesterase to an Organophosphorus Hydrolase and Confers Insecticide Resistance on a Blowfly," *Proc. Natl. Acad. Sci. USA* 94:7464-7468.

Newcomb et al. (1997) "cDNA Cloning, Baculovirus-Expression and Kinetic Properties of the Esterase, E3, Involved in Organophosphorus Resistance in *Lucilia cuprina*," *Insect Biochem. Molec. Biol.* 27(1):15-25.

Oakeshott et al. (1999) "Carboxyl/Cholinesterases: A Case Study of the Evolution of a Successful Multigene Family," *BioEssays* 21:1031-1042.

Oakeshott et al. (1993) "Evolutionary Genetics of *Drosophila* Esterases," *Genetica* 90:239-268.

Ordentlich et al. (1998) "Functional Characteristics of the Oxyanion Hole in Human Acetylcholinesterase," *J. Biol. Chem.* 273:19509-19517.

Ordentlich et al (1996) "The Architecture of Human Acetylcholinesterase Active Center Probed by Interactions with Selected Organophosphate Inhibitors," *J. Biol. Chem.* 271:11953-11962.

Ordentlich et al. (1995) "Contribution of Aromatic Moieties of Tyrosine 133 and of the Anionic Subsite Tryptophan 86 to Catalytic Efficiency and Allosteric Modulation of Acetylcholinesterase," *J. Biol. Chem.* 270:2082-2091.

Ordentlich et al. (1993) "Dissection of the Human Acetylcholinesterase Active Center Determinants of Substrate Specificity," *J. Biol. Chem.* 268:17083-17095.

Patten et al. (1997) "Applications of DNA Shuffling to Pharmaceuticals and Vaccines," *Curr. Opin. Biotechnol.* 8:724-733.

Petrikovics et al. (2000) "Long Circulating Liposomes Encapsulating Organophosphorus Acid Anhydrolase in Diisopropylfluorophosphate Antagonism," *Toxicol. Sci.* 57:16-21.

Petrikovics et al. (2000) "In Vitro Studies on Sterically Stabilized Liposomes (SL) as Enzyme Carriers in Organophosphorus (OP) Antagonism," *Drug Delivery* 7:83-89.

Picollo et al. (2000) "Resistance to Insecticides and Effect of Synergists on Permethrin Toxicity in *Pediculus capitis* (Anoplura: Pediculidae) from Buenos Aires," *J. Med. Entomol.* 37(5):721-725.

Qian et al. (1993) "Key Active Site Residues in the Inhibition of Acetylcholinesterases by Soman," *FEBS Lett.* 336:263-266.

Robin et al (1996) "Duplication and Divergence of the Genes of the α-Esterase Cluster of *Drosophila melangaster*," *J. Mol. Evol.* 43:241-252.

Robin et al. (2000) "Reconstructing the Diversification of Alpha-Esterases: Comparing the Gene Clusters of *Drosophila buzzatii* and *D. melanogaster*," *J. Mol. Evol.* 51:149-160.

Rodriguez et al. (Sep. 2001) "Detection of Insecticide Resistance in *Aedes aegypti* (Diptera: Culicidae) from Cuba and Venezuela," *J. Med. Entomol.* 38(5):623-628.

Shafferman et al. (1992) "Substrate Inhibition of Acetylcholinesterase: Residues Affecting Signal Transduction from the Surface to the Catalytic Center," *EMBO J.* 11:3561-3568.

Small et al. (2000) "Molecular Characterization of the Amplified Carboxylesterase Gene Associated with Organophosphorus insecticide resistance in the Brown Planthopper, *Nilaparvata lugens*," *Insect Mol. Biol.* 9(6):647-653.

Sussman et al. (1991) "Atomic Structure of Acetylcholinesterase from *Torpedo californica*: A Prototypic Acetylcholine-Binding Protein," *Science* 253:872-879.

Thomas et al. (1999) "Homology Model of Juvenile Hormone Esterase from the Crop Pest, *Heliothis virescens*," *Proteins* 34:184-196.

Valles et al. (Apr. 2001) "Purification and Characterization of Trans-Permethrin Metabolizing Microsomal Esterases from Workers of the Eastern Subterranean Termite, *Reticulitermes flavipes* (Kollar)," *Insect Biochem. Mol. Biol.* 31:715-725.

Villatte et al. (2000) "A High Number of Mutations in Insect Acetylcholinesterase May Provide Insecticide Resistance," *Pest. Biochem Physiol.* 67:95-102.

Walsh et al. (Oct. 2001) "Identification and Characterization of Mutations in Housefly (*Musca domestica*) Acetylcholinesterase Involved in Insecticide Resistance," *Biochem. J.* 359:175-181.

Yao et al. (1997) "Characterization of the Acetylcholinesterase Gene from Insecticide-Resistant Houseflies (*Musca domestica*)," *Clin. J. Biotechnol.* 13:177-183.

Zhu et al. (1999) "Differential mRNA Expression Levels and Gene Sequences of a Putative Carboxylesterase-Like Enzyme from Two Strains of the Parasitoid *Anisopteromalus calandrae* (Hymenoptera: Pteromalidae)," *Insect Biochem. Molec. Biol.* 29:417-425.

Russell et al. (1996) Molecular Cloning of an α-esterase Gene Cluster on Chromosome 3R of *Drosophila melanogaster*. Insect Biochem. Molec. Biol. 26(3):235-247.

\* cited by examiner

```
E3      1  MNFNVSLMEKLKWKIKCIENKFLNYRLTTNETVVAETEYGKVKGVKRLTVYDDSYYSFEG
AChE    1  ....................ADDDSELLVNTKSGKVMRT.RIPVLSSHISAFLG

E3     61  IPYAQPPVGELRFKAPQRPTPWDGVRDCCNHKDKS...VQVDFIT.......G.KVCGSE
AChE   34  IPFAEPPVGNMRFRRPEPKKPWSGVWNASTYPNNCQQYVDEQFPGFPGSEMWNPNREMSE

E3    110  DCLYLSVYTNNLNPETK....RPVLVYIHGGGFIIGENHRDMYGPDYFI.KKDVVLINIQ
AChE   94  DCLYLNIWVPSPRPKSAT.....VMLWIYGGGFYSGSSTLDVYNGKYLAYTEEVVLVSLS

E3    165  YRLGALGFLSLNSEDLNVPGNAGLKDQVMALRWIKNNCANFGGNPDNITVFGESAGAAST
AChE  149  YRVGAFGFLALHGSQEA.PGNMGLLDQRMALQWVHDNIQFFGGDPKTVTLFGESAGRASV

E3    225  HYMMLTEQTRGLFHRGILMSGNAICPWANTQ.CQHRAFTIAKLAGYKGEDNDKD.VLEFL
AChE  208  GMHILSPGSRDLFRRAILQSGSPNCPWASVSVAEGRRRAVELRRNLNCNLNSDEDLIQCL

E3    283  MKAKPQDLIKLEEKVLTLEERTNKVMFPFGPTVEPYQTADCVLPKHPREMVKTAWGNSIP
AChE  268  REKKPQELIDVE...WNVLPFDSIFRFSFVPVID.....GEFFPTSLESMLNAGNFKKTQ

E3    343  TMMGNTSYEGLFFTSILKQMPMLVKELETCVNFVPSELADAERTAPET...LEMGAKIKK
AChE  320  ILLGVNKDEGSFF..LLYGAPGFSKDSESKIS.REDFMSGVKLSVPHANDLGLDAVTLQY

E3    400  AHVTGET...PTADNFMDLCSHIYFWFPMHRLLQLRFNHTSGTPVYLYRFDFDSEDLINP
AChE  377  TDWMDDNNGIKNRDGLDDIVGNHNVICPLMHFVNKYTKFGNGTYLYFFNHR.ASNLVWPE

E3    457  YRIMRSGRGVKGVSHADELTYFFWNQLAKRMPKESREYKTIERMTGIWIQFATTGNPYSN
AChE  436  WM.........GVIHGYEIEFVFGLPLVKELNYTAEEEALSRRIMHYWATFAKTGNPNEP

E3    517  EIEG...........MENVSWDPIKKSD....EVYKCLNISDELKMIDVPEMDK.IKQW
AChE  487  HSQESKWPLFTTKEQKFIDLNTEPIKVHQRLRVQMCVFWNQFLPKLLNATETIDEAERQW

E3    560  ESMFEKHRDLF*..................
AChE  547  KTEFHRWSSYMMHWKNQFDQYSRHENCAEL
```

Figure 1

SEQUENCE LISTING

```
<160> NUMBER OF SEQ ID NOS: 3

<210> SEQ ID NO 1
<211> LENGTH: 570
<212> TYPE: PRT
<213> ORGANISM: Lucilia cuprina

<400> SEQUENCE: 1

Met Asn Phe Asn Val Ser Leu Met Glu Lys Leu Lys Trp Lys Ile Lys
1               5                   10                  15

Cys Ile Glu Asn Lys Phe Leu Asn Tyr Arg Leu Thr Thr Asn Glu Thr
            20                  25                  30

Val Val Ala Glu Thr Glu Tyr Gly Lys Val Lys Gly Val Lys Arg Leu
        35                  40                  45

Thr Val Tyr Asp Asp Ser Tyr Tyr Ser Phe Glu Gly Ile Pro Tyr Ala
    50                  55                  60

Gln Pro Pro Val Gly Glu Leu Arg Phe Lys Ala Pro Gln Arg Pro Thr
65                  70                  75                  80

Pro Trp Asp Gly Val Arg Asp Cys Cys Asn His Lys Asp Lys Ser Val
                85                  90                  95

Gln Val Asp Phe Ile Thr Gly Lys Val Cys Gly Ser Glu Asp Cys Leu
            100                 105                 110

Tyr Leu Ser Val Tyr Thr Asn Asn Leu Asn Pro Glu Thr Lys Arg Pro
        115                 120                 125

Val Leu Val Tyr Ile His Gly Gly Gly Phe Ile Ile Gly Glu Asn His
    130                 135                 140

Arg Asp Met Tyr Gly Pro Asp Tyr Phe Ile Lys Lys Asp Val Val Leu
145                 150                 155                 160

Ile Asn Ile Gln Tyr Arg Leu Gly Ala Leu Gly Phe Leu Ser Leu Asn
                165                 170                 175

Ser Glu Asp Leu Asn Val Pro Gly Asn Ala Gly Leu Lys Asp Gln Val
            180                 185                 190

Met Ala Leu Arg Trp Ile Lys Asn Asn Cys Ala Asn Phe Gly Gly Asn
        195                 200                 205

Pro Asp Asn Ile Thr Val Phe Gly Glu Ser Ala Gly Ala Ala Ser Thr
    210                 215                 220

His Tyr Met Met Leu Thr Glu Gln Thr Arg Gly Leu Phe His Arg Gly
```

```
                225                 230                 235                 240

Ile Leu Met Ser Gly Asn Ala Ile Cys Pro Trp Ala Asn Thr Gln Cys
                245                 250                 255

Gln His Arg Ala Phe Thr Leu Ala Lys Leu Ala Gly Tyr Lys Gly Glu
                260                 265                 270

Asp Asn Asp Lys Asp Val Leu Glu Phe Leu Met Lys Ala Lys Pro Gln
                275                 280                 285

Asp Leu Ile Lys Leu Glu Glu Lys Val Leu Thr Leu Glu Glu Arg Thr
            290                 295                 300

Asn Lys Val Met Phe Pro Phe Gly Pro Thr Val Glu Pro Tyr Gln Thr
305                 310                 315                 320

Ala Asp Cys Val Leu Pro Lys His Pro Arg Glu Met Val Lys Thr Ala
                    325                 330                 335

Trp Gly Asn Ser Ile Pro Thr Met Met Gly Asn Thr Ser Tyr Glu Gly
                340                 345                 350

Leu Phe Phe Thr Ser Ile Leu Lys Gln Met Pro Met Leu Val Lys Glu
                355                 360                 365

Leu Glu Thr Cys Val Asn Phe Val Pro Ser Glu Leu Ala Asp Ala Glu
            370                 375                 380

Arg Thr Ala Pro Glu Thr Leu Glu Met Gly Ala Lys Ile Lys Lys Ala
385                 390                 395                 400

His Val Thr Gly Glu Thr Pro Thr Ala Asp Asn Phe Met Asp Leu Cys
                    405                 410                 415

Ser His Ile Tyr Phe Trp Phe Pro Met His Arg Leu Leu Gln Leu Arg
                420                 425                 430

Phe Asn His Thr Ser Gly Thr Pro Val Tyr Leu Tyr Arg Phe Asp Phe
                435                 440                 445

Asp Ser Glu Asp Leu Ile Asn Pro Tyr Arg Ile Met Arg Ser Gly Arg
            450                 455                 460

Gly Val Lys Gly Val Ser His Ala Asp Glu Leu Thr Tyr Phe Phe Trp
465                 470                 475                 480

Asn Gln Leu Ala Lys Arg Met Pro Lys Glu Ser Arg Glu Tyr Lys Thr
                    485                 490                 495

Ile Glu Arg Met Thr Gly Ile Trp Ile Gln Phe Ala Thr Thr Gly Asn
                500                 505                 510

Pro Tyr Ser Asn Glu Ile Glu Gly Met Glu Asn Val Ser Trp Asp Pro
                515                 520                 525

Ile Lys Lys Ser Asp Glu Val Tyr Lys Cys Leu Asn Ile Ser Asp Glu
            530                 535                 540

Leu Lys Met Ile Asp Val Pro Glu Met Asp Lys Ile Lys Gln Trp Glu
545                 550                 555                 560

Ser Met Phe Glu Lys His Arg Asp Leu Phe
                    565                 570

<210> SEQ ID NO 2
<211> LENGTH: 572
<212> TYPE: PRT
<213> ORGANISM: Drosophila melanogaster

<400> SEQUENCE: 2

Met Asn Lys Asn Leu Gly Phe Val Glu Arg Leu Arg Gly Arg Leu Lys
1               5                   10                  15

Thr Ile Glu His Lys Val Gln Gln Tyr Arg Gln Ser Thr Asn Glu Thr
                20                  25                  30
```

-continued

```
Val Val Ala Asp Thr Glu Tyr Gly Gln Val Arg Gly Ile Lys Arg Leu
         35                  40                  45

Ser Leu Tyr Asp Val Pro Tyr Phe Ser Phe Glu Gly Ile Pro Tyr Ala
     50                  55                  60

Gln Pro Pro Val Gly Glu Leu Arg Phe Lys Ala Pro Gln Arg Pro Ile
 65                  70                  75                  80

Pro Trp Glu Gly Val Arg Asp Cys Ser Gln Pro Lys Asp Lys Ala Val
                 85                  90                  95

Gln Val Gln Phe Val Phe Asp Lys Val Glu Gly Ser Glu Asp Cys Leu
                100                 105                 110

Tyr Leu Asn Val Tyr Thr Asn Val Lys Pro Asp Lys Ala Arg Pro
         115                 120                 125

Val Met Val Trp Ile His Gly Gly Phe Ile Ile Gly Glu Ala Asn
 130                 135                 140

Arg Glu Trp Tyr Gly Pro Asp Tyr Phe Met Lys Glu Asp Val Val Leu
145                 150                 155                 160

Val Thr Ile Gln Tyr Arg Leu Gly Ala Leu Gly Phe Met Ser Leu Lys
                165                 170                 175

Ser Pro Glu Leu Asn Val Pro Gly Asn Ala Gly Leu Lys Asp Gln Val
                180                 185                 190

Leu Ala Leu Lys Trp Ile Lys Asn Asn Cys Ala Ser Phe Gly Gly Asp
         195                 200                 205

Pro Asn Cys Ile Thr Val Phe Gly Glu Ser Ala Gly Gly Ala Ser Thr
         210                 215                 220

His Tyr Met Met Leu Thr Asp Gln Thr Gln Gly Leu Phe His Arg Gly
225                 230                 235                 240

Ile Leu Gln Ser Gly Ser Ala Ile Cys Pro Trp Ala Tyr Asn Gly Asp
                245                 250                 255

Ile Thr His Asn Pro Tyr Arg Ile Ala Lys Leu Val Gly Tyr Lys Gly
                260                 265                 270

Glu Asp Asn Asp Lys Asp Val Leu Glu Phe Leu Gln Asn Val Lys Ala
            275                 280                 285

Lys Asp Leu Ile Arg Val Glu Asn Val Leu Thr Leu Glu Glu Arg
         290                 295                 300

Met Asn Lys Ile Met Phe Arg Phe Gly Pro Ser Leu Glu Pro Phe Ser
305                 310                 315                 320

Thr Pro Glu Cys Val Ile Ser Lys Pro Pro Lys Glu Met Met Lys Thr
                325                 330                 335

Ala Trp Ser Asn Ser Ile Pro Met Phe Ile Gly Asn Thr Ser Tyr Glu
            340                 345                 350

Gly Leu Leu Trp Val Pro Glu Val Lys Leu Met Pro Gln Val Leu Gln
         355                 360                 365

Gln Leu Asp Ala Gly Thr Pro Phe Ile Pro Lys Glu Leu Leu Ala Thr
    370                 375                 380

Glu Pro Ser Lys Glu Lys Leu Asp Ser Trp Ser Ala Gln Ile Arg Asp
385                 390                 395                 400

Val His Arg Thr Gly Ser Glu Ser Thr Pro Asp Asn Tyr Met Asp Leu
                405                 410                 415

Cys Ser Ile Tyr Tyr Phe Val Phe Pro Ala Leu Arg Val Val His Ser
            420                 425                 430

Arg His Ala Tyr Ala Ala Gly Ala Pro Val Tyr Phe Tyr Arg Tyr Asp
         435                 440                 445

Phe Asp Ser Glu Glu Leu Ile Phe Pro Tyr Arg Ile Met Arg Met Gly
```

```
             450                 455                 460
Arg Gly Val Lys Gly Val Ser His Ala Asp Asp Leu Ser Tyr Gln Phe
465                 470                 475                 480

Ser Ser Leu Leu Ala Arg Arg Leu Pro Lys Glu Ser Arg Glu Tyr Arg
                485                 490                 495

Asn Ile Glu Arg Thr Val Gly Ile Trp Thr Gln Phe Ala Ala Thr Gly
                500                 505                 510

Asn Pro Tyr Ser Glu Lys Ile Asn Gly Met Asp Thr Leu Thr Ile Asp
                515                 520                 525

Pro Val Arg Lys Ser Asp Glu Val Ile Lys Cys Leu Asn Ile Ser Asp
530                 535                 540

Asp Leu Lys Phe Ile Asp Leu Pro Glu Trp Pro Lys Leu Lys Val Trp
545                 550                 555                 560

Glu Ser Leu Tyr Asp Asp Asn Lys Asp Leu Leu Phe
                565                 570
```

<210> SEQ ID NO 3
<211> LENGTH: 576
<212> TYPE: PRT
<213> ORGANISM: Torpedo californica

<400> SEQUENCE: 3

```
Ala Asp Asp Ser Glu Leu Leu Val Asn Thr Lys Ser Gly Lys Val
1               5                   10                  15

Met Arg Thr Arg Ile Pro Val Leu Ser Ser His Ile Ser Ala Phe Leu
                20                  25                  30

Gly Ile Pro Phe Ala Glu Pro Val Gly Asn Met Arg Phe Arg
                35                  40                  45

Pro Glu Pro Lys Lys Pro Trp Ser Gly Val Trp Asn Ala Ser Thr Tyr
                50                  55                  60

Pro Asn Asn Cys Gln Gln Tyr Val Asp Glu Gln Phe Pro Gly Phe Pro
65                  70                  75                  80

Gly Ser Glu Met Trp Asn Pro Asn Arg Glu Met Ser Glu Asp Cys Leu
                85                  90                  95

Tyr Leu Asn Ile Trp Val Pro Ser Pro Arg Pro Lys Ser Ala Thr Val
                100                 105                 110

Met Leu Trp Ile Tyr Gly Gly Gly Phe Tyr Ser Gly Ser Ser Thr Leu
                115                 120                 125

Asp Val Tyr Asn Gly Lys Tyr Leu Ala Tyr Thr Glu Glu Val Val Leu
130                 135                 140

Val Ser Leu Ser Tyr Arg Val Gly Ala Phe Gly Phe Leu Ala Leu His
145                 150                 155                 160

Gly Ser Gln Glu Ala Pro Gly Asn Met Gly Leu Leu Asp Gln Arg Met
                165                 170                 175

Ala Leu Gln Trp Val His Asp Asn Ile Gln Phe Phe Gly Gly Asp Pro
                180                 185                 190

Lys Thr Val Thr Leu Phe Gly Glu Ser Ala Gly Arg Ala Ser Val Gly
                195                 200                 205

Met His Ile Leu Ser Pro Gly Ser Arg Asp Leu Phe Arg Arg Ala Ile
                210                 215                 220

Leu Gln Ser Gly Ser Pro Asn Cys Pro Trp Ala Ser Val Ser Val Ala
225                 230                 235                 240

Glu Gly Arg Arg Arg Ala Val Glu Leu Arg Arg Asn Leu Asn Cys Asn
                245                 250                 255
```

-continued

```
Leu Asn Ser Asp Glu Asp Leu Ile Gln Cys Leu Arg Glu Lys Lys Pro
            260                 265                 270

Gln Glu Leu Ile Asp Val Glu Trp Asn Val Leu Pro Phe Asp Ser Ile
        275                 280                 285

Phe Arg Phe Ser Phe Val Pro Val Ile Asp Gly Glu Phe Phe Pro Thr
    290                 295                 300

Ser Leu Glu Ser Met Leu Asn Ala Gly Asn Phe Lys Lys Thr Gln Ile
305                 310                 315                 320

Leu Leu Gly Val Asn Lys Asp Glu Gly Ser Phe Phe Leu Leu Tyr Gly
                325                 330                 335

Ala Pro Gly Phe Ser Lys Asp Ser Glu Ser Lys Ile Ser Arg Glu Asp
            340                 345                 350

Phe Met Ser Gly Val Lys Leu Ser Val Pro His Ala Asn Asp Leu Gly
        355                 360                 365

Leu Asp Ala Val Thr Leu Gln Tyr Thr Asp Trp Met Asp Asp Asn Asn
    370                 375                 380

Gly Ile Lys Asn Arg Asp Gly Leu Asp Asp Ile Val Gly Asn His Asn
385                 390                 395                 400

Val Ile Cys Pro Leu Met His Phe Val Asn Lys Tyr Thr Lys Phe Gly
                405                 410                 415

Asn Gly Thr Tyr Leu Tyr Phe Phe Asn His Arg Ala Ser Asn Leu Val
            420                 425                 430

Trp Pro Glu Trp Met Gly Val Ile His Gly Tyr Glu Ile Glu Phe Val
        435                 440                 445

Phe Gly Leu Pro Leu Val Lys Glu Leu Asn Tyr Thr Ala Glu Glu Glu
    450                 455                 460

Ala Leu Ser Arg Arg Ile Met His Tyr Trp Ala Thr Phe Ala Lys Thr
465                 470                 475                 480

Gly Asn Pro Asn Glu Pro His Ser Gln Glu Ser Lys Trp Pro Leu Phe
                485                 490                 495

Thr Thr Lys Glu Gln Lys Phe Ile Asp Leu Asn Thr Glu Pro Ile Lys
            500                 505                 510

Val His Gln Arg Leu Arg Val Gln Met Cys Val Phe Trp Asn Gln Phe
        515                 520                 525

Leu Pro Lys Leu Leu Asn Ala Thr Glu Thr Ile Asp Glu Ala Glu Arg
    530                 535                 540

Gln Trp Lys Thr Glu Phe His Arg Trp Ser Ser Tyr Met Met His Trp
545                 550                 555                 560

Lys Asn Gln Phe Asp Gln Tyr Ser Arg His Glu Asn Cys Ala Glu Leu
                565                 570                 575
```

DEGRADATION OF HYDROPHOBIC ESTER PESTICIDES AND TOXINS

CROSS REFERENCE TO RELATED APPLICATIONS

This application is a National Stage Application of PCT International Application No. PCT/AU02/00114, filed Feb. 6, 2002.

FIELD OF THE INVENTION

This invention relates to enzymes and methods for degrading hydrophobic ester pesticides and toxins. In particular, the present invention relates to the use of insect esterases, such as α-carboxylesterases, and mutants thereof, in the bioremediation of pyrethroid residues contaminating the environment and horticultural commodities.

BACKGROUND OF THE INVENTION

Pyrethroids constitute a major class of chemical pesticides. They are synthetic analogues of the natural pyrethrins, which are produced in the flowers of the pyrethrum plant (*Tanacetum cinerarifolium*). Modification of their structure has yielded compounds that retain the intrinsically modest vertebrate toxicity of the natural products but are both more stable and more potent as pesticides. In the thirty years since their introduction they have risen to about 10-20% of insecticide sales worldwide and they are projected to retain substantial market share into the forseeable future. They are now widely used across agricultural production and processing systems in many countries and have caused residue incidents in diverse commodities ranging from cotton and horticulture through to wool.

Residues of pyrethroid pesticides are undesirable contaminants of the environment and a range of commodities. They are undesirable because of the broad target range of the pesticide across invertebrates and their significant toxicity to vertebrates, although they are generally considered to be amongst the safest pesticides to mammals. Areas of particular sensitivity include contamination of soil, irrigation tailwater that is re-cycled, used by irrigators downstream or simply allowed to run off-farm, and residues above permissible levels in horticultural exports. Animal industries also have problems with pesticide-contaminated commodities arising through either their own pesticide use or their reliance on crop products and by-products as fodder. Processing wastes from food processing plants, carpet dye baths and animal dips are also contaminated, sometimes quite heavily, with pesticide residues. Bioremediation strategies are therefore required for eliminating or reducing these pesticide residues.

One proposed bioremediation strategy involves the use of enzymes capable of immobilising or degrading the pesticide residues. Such enzymes may be employed, for example, in bioreactors through which contaminated water could be passed, or in washing solutions after post-harvest disinfestation of fruit, vegetables or animal products to reduce residue levels and withholding times. Suitable enzymes for degrading pesticide residues include OP hydrolases from bacteria, vertebrates and organophosphate (OP) resistant insects. It is desirable that the hydrolytic enzymes degrade the pesticide residues at a rapid rate.

Organophosphate resistance in the sheep blowfly, *Lucilia cuprina*, is conferred by two different mutations in the gene encoding carboxylesterase E3. The two mutant enzymes differ in their substrate specificities but between them can detoxify two major subtypes of OPs. The E3 gene from *L. cuprina* was cloned by Newcomb et al. (1997) and, using a combination of DNA sequencing, baculovirus expression and in vitro mutagenesis, these workers identified the two resistance mutations. One is an Asp for Gly substitution at residue 137 in the oxyanion hole region of the active site (Newcomb et al., 1997). The other is a Leu for Trp substitution at residue 251 in the substrate-binding region (Campbell et al., 1998), which results in an increase in malathion carboxylesterase activity as well as the acquisition of OP hydrolase activity.

There is a need for methods and enzymes which can be used for the bioremediation of, for example, soils, foodstuff and water samples contaminated with hydrophobic ester pesticides and toxins.

SUMMARY OF THE INVENTION

The present inventors have now found that insect esterases, and mutants thereof, are able to hydrolyse hydrophobic ester pesticides and toxins such as pyrethroids. The activity of the insect esterases, and mutants thereof, show a degree of chiral specificity, which differed between mutants. It is therefore possible to provide a suite of insect esterases, or mutants thereof, that are able to degrade hydrophobic ester pesticides and toxins that can act, alone or together, as effective bioremediation agents for hydrophobic ester pesticides and toxins such as pyrethroids.

Accordingly, in a first aspect, the present invention provides a method of eliminating or reducing the concentration of a hydrophobic ester pesticide or toxin in a sample, the method comprising contacting the sample with an insect esterase, or a mutant thereof.

In a preferred embodiment of the first aspect, the insect esterase is a member of the carboxyl/cholinesterase multigene family of enzymes. More preferably, the insect esterase is an α-carboxylesterase. Even more preferably, the insect esterase is a member of the α-carboxylesterase cluster which forms a sub-clade within this multi-gene family (Oakeshott et al., 1999). Esterases which form this sub-clade include at least α-carboxylesterases which can be isolated from species of Diptera, Hemiptera and Hymenoptera. Specific enzymes which are found in this sub-clade include, but are not limited to, the E3 or EST23 esterases. However, orthologous esterases of E3 and EST23 from other insect species can also be used in the methods of the present invention.

Preferably, the α-carboxylesterases can be isolated from a species of Diptera. Accordingly, examples of preferred α-carboxylesterases for use in the present invention are the E3 esterase (SEQ ID NO:1) which is derived from *Lucilia cuprina*, or the EST23 esterase (SEQ ID NO:2) which is derived from *Drosophila melanogaster*.

In a further preferred embodiment, the mutant insect esterase has a mutation(s) in the oxyanion hole, acyl binding pocket or anionic site regions of the active site, or any combination thereof.

In a further preferred embodiment, the mutant α-carboxylesterase is selected from the group consisting of: E3G137R, E3G137H, E3W251L, E3W251S, E3W251G, E3W251T, E3W251A, E3W251L/F309L, E3W251L/G137D, E3W251L/P250S, E3F309L, E3Y148F, E3E217M, E3F354W, E3F354L, and EST23W251L. Preferably, the mutant α-carboxylesterase is E3W251L, E3F309L, E3W251L/F309L or EST23W251L.

In another preferred embodiment of the first aspect, the α-carboxylesterase, or mutant thereof, has a sequence selected from the group consisting of:

i) a sequence as shown in SEQ ID NO:1, ii) a sequence as shown in SEQ ID NO:2, and iii) a sequence which is at least 40% identical to i) or ii) which is capable of hydrolysing a hydrophobic ester pesticide or toxin. More preferably, the polypeptide is at least 50% identical, more preferably at least 60% identical, more preferably at least 70% identical, more preferably at least 80% identical, and more preferably at least 90% identical, more preferably at least 95% identical, and even more preferably at least 97% identical to i) or ii).

As the skilled addressee would be aware, the method of the first aspect can be performed using more than one insect esterase, or mutants thereof. This is particularly the case where different insect esterases, or mutants thereof, have different hydrolytic activity for different stereo-isomers of the hydrophobic ester pesticide or toxin.

The hydrophobic ester pesticide or toxin can be any molecule which is hydrophobic in nature, contains an ester group and has some level of toxicity towards living organisms. A particularly preferred hydrophobic ester pesticide or toxin is a pyrethroid. The pyrethroid can be a Type I or Type II pyrethroid. Preferably, the Type I pyrethroid is selected from the group consisting of: 1S/1R trans permethrin, 1S/1R cis permethrin, NRDC157 1S cis, and NRDC157 1R cis. Preferably, the Type II pyrethroid is deltamethrin.

Preferably, the sample is a soil sample, a water sample or a biological sample. Preferred biological samples include matter derived from plants such as seeds, vegetables or fruits, as well as matter derived from animals such as meat.

Preferably, the method is performed in a liquid containing environment.

The sample can be exposed to the insect esterase, or mutant thereof, by any appropriate means. This includes providing the insect esterase, or mutant thereof, directly to the sample, with or without carriers or excipients etc. The insect esterase, or mutant thereof, can also be provided in the form of a host cell, typically a microorganism such as a bacterium or a fungus, which expresses a polynucleotide encoding the insect esterase, or mutant thereof.

The insect esterase, or mutant thereof, can also be as provided a polymeric sponge or foam, the foam or sponge comprising the insect esterase, or mutant thereof, immobilized on a polymeric porous support.

Preferably, the porous support comprises polyurethane.

In a preferred embodiment, the sponge or foam further comprises carbon embedded or integrated on or in the porous support.

It is envisaged that the use of a surfactant in the method of the present invention may liberate hydrophobic ester pesticides and/or toxins from any, for example, sediment in the sample. Thus increasing efficiency of the method of the present invention. Accordingly, in another preferred embodiment, the method comprises the presence of a surfactant when the hydrophobic ester pesticide or toxin is contacted with the insect esterase, or mutant thereof. More preferably, the surfactant is a biosurfactant.

Further, hydrophobic ester pesticide or toxin in a sample can also be degraded by exposing the sample to a transgenic plant which produces the insect esterase, or mutant thereof.

In a second aspect the present invention provides a substantially purified polypeptide which is a mutant of an insect esterase, wherein one or more mutations are within a region of the esterase selected from the group consisting of: oxyanion hole, acyl binding pocket and anionic site, wherein the mutant insect esterase is capable of hydrolysing a hydrophobic ester pesticide or toxin, with the proviso that the mutant insect esterase is not E3W251L, E3W251S, E3W251G or E3G137D.

Preferably, the insect esterase is an α-carboxylesterase.

Preferably, the polypeptide is selected from the group consisting of:

i) a mutant of a sequence as shown in SEQ ID NO:1, and ii) a mutant of sequence as shown in SEQ ID NO:2, wherein the mutant is at least 40% identical to at least one of SEQ ID NO's:1 or 2. More preferably, the mutant is at least 80% identical to at least one of SEQ ID NO's:1 or 2. Even more preferably, the mutant is at least 90% identical to at least one of SEQ ID NO's:1 or 2.

Preferably, the mutation is a point mutation.

Preferably, the polypeptide selected from the group consisting of: E3G137R, E3G137H, E3W251T, E3W251A, E3W251L1309L, E3W251L/G137D, E3W251L/P250S, E3F309L, E3Y148F, E3E217M, E3F354W, E3F354L, EST23W251L.

In a third aspect, the present invention provides a fusion polypeptide comprising a polypeptide according to the second aspect fused to at least one other polypeptide sequence.

In a fourth aspect the present invention provides an isolated polynucleotide encoding a polypeptide according to the second or third aspects.

In a fifth aspect the present invention provides a vector for replication and/or expression of a polynucleotide according to the fourth aspect.

In a sixth aspect the present invention provides a host cell transformed or transfected with the vector of the fifth aspect.

In a seventh aspect the present invention provides a composition for hydrolysing a hydrophobic ester pesticide or toxin, the composition comprising a polypeptide according to the second or third aspects, and one or more acceptable carriers.

In an eighth aspect the present invention provides a method for generating and selecting an enzyme that hydrolyses a hydrophobic ester pesticide or toxin, the method comprising (i) introducing one or more mutations into an insect esterase, or an insect esterase that has already been mutated, and (ii) determining the ability of the mutant insect esterase to hydrolyse a hydrophobic ester pesticide or toxin.

Preferably, the one or more mutations enhances hydrolytic activity and/or alters the stereospecificty of the esterase.

Such one or more mutations can be introduced by a variety of techniques known to the skilled addressee. These techniques include, but are not limited to, site directed mutagenesis, random mutagenesis, or the use of DNA shuffling in in vitro evolution techniques, each of which are performed on a polynucleotide encoding the insect esterase or insect esterase that has already been mutated.

In a preferred embodiment of the eighth aspect, the insect esterase is an α-carboxylesterase. More preferably, the α-carboxylesterase is an E3 or EST23 esterase. More preferably, the α-carboxylesterase has a sequence selected from the group consisting of:

i) a sequence as shown in SEQ D NO:1, ii) a sequence as shown in SEQ ID NO:2, and iii) a sequence which is at least 40% identical to i) or ii). More preferably, the polypeptide is at least 50% identical, more preferably at least 60% identical, more preferably at least 70% identical, more preferably at least 80% identical, and more preferably at least 90% identical, more preferably at least 95% identical, and even more preferably at least 97% identical to i) or ii).

Preferably, the one or more mutations are within a region of the esterase selected from the group consisting of: oxyanion hole, acyl binding pocket and anionic site.

In a further preferred embodiment, the insect esterase that has already been mutated is selected from the group consisting of: E3G137R, E3G137H, E3W251L, E3W251S, E3W251G, E3W251T, E3W251A, E3W251L/F309L, E3W251L/G137D, E3W251L/P250S, E3F309L, E3Y148F, E3E217M, E3F354W, E3F354L, and EST23W251L.

In a further preferred embodiment of the eighth aspect, the mutation is a point mutation.

In a ninth aspect the present invention provides an enzyme obtained by a method according to the eighth aspect.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting example and with reference to the accompanying figures.

BRIEF DESCRIPTION OF THE ACCOMPANYING DRAWINGS

FIG. 1: Amino acid sequence alignment of the E3 (SEQ ID NO:1) and *Torpedo californica* acetylcholinesterase (SEQ ID NO:3) enzymes. The sequence around the active site serine and residues Gly137, Trp251 and Phe309 are shown in bold and underlined.

FIG. 2: Proposed configuration of active site of LcE3 carboxylesterase in an acylation reaction.

Figure 3:
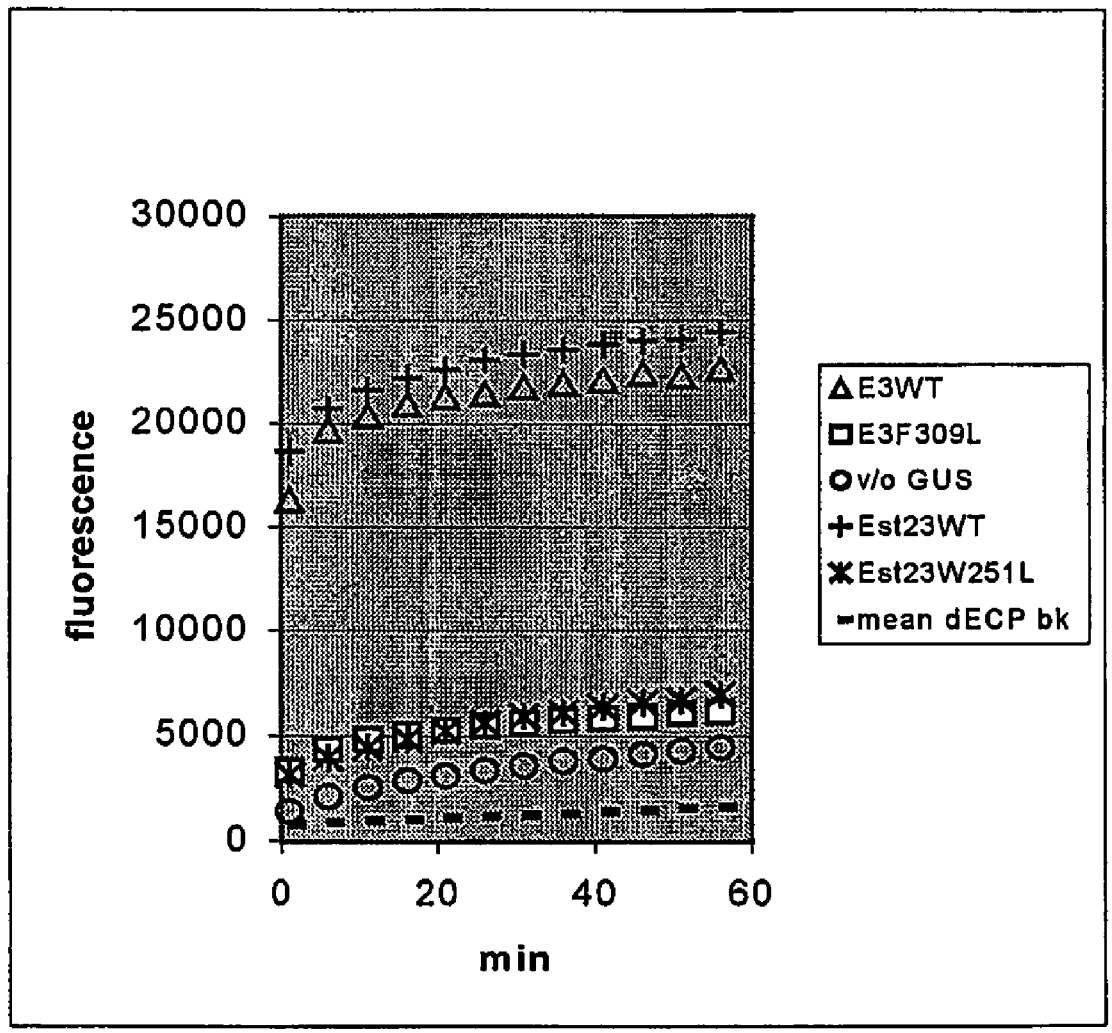

FIG. 3: Results of representative titration experiments performed on cell extracts containing baculovirus expressed esterases.

Figure 4:
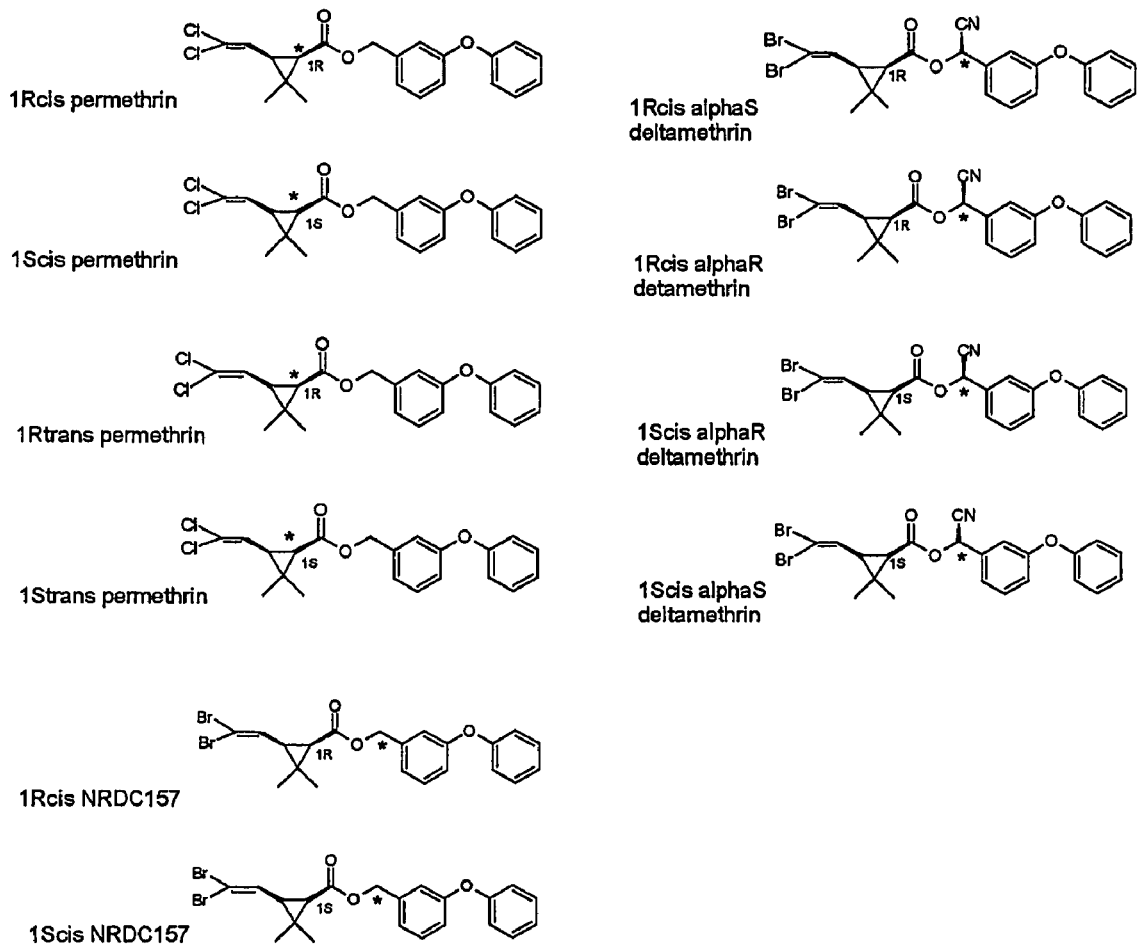

FIG. 4: Molecular structures for 1R/S cis and trans permethrin, 1R/S cis and trans NRDC157 and the four stereoisomers of cis deltamethrin.

Figure 5:
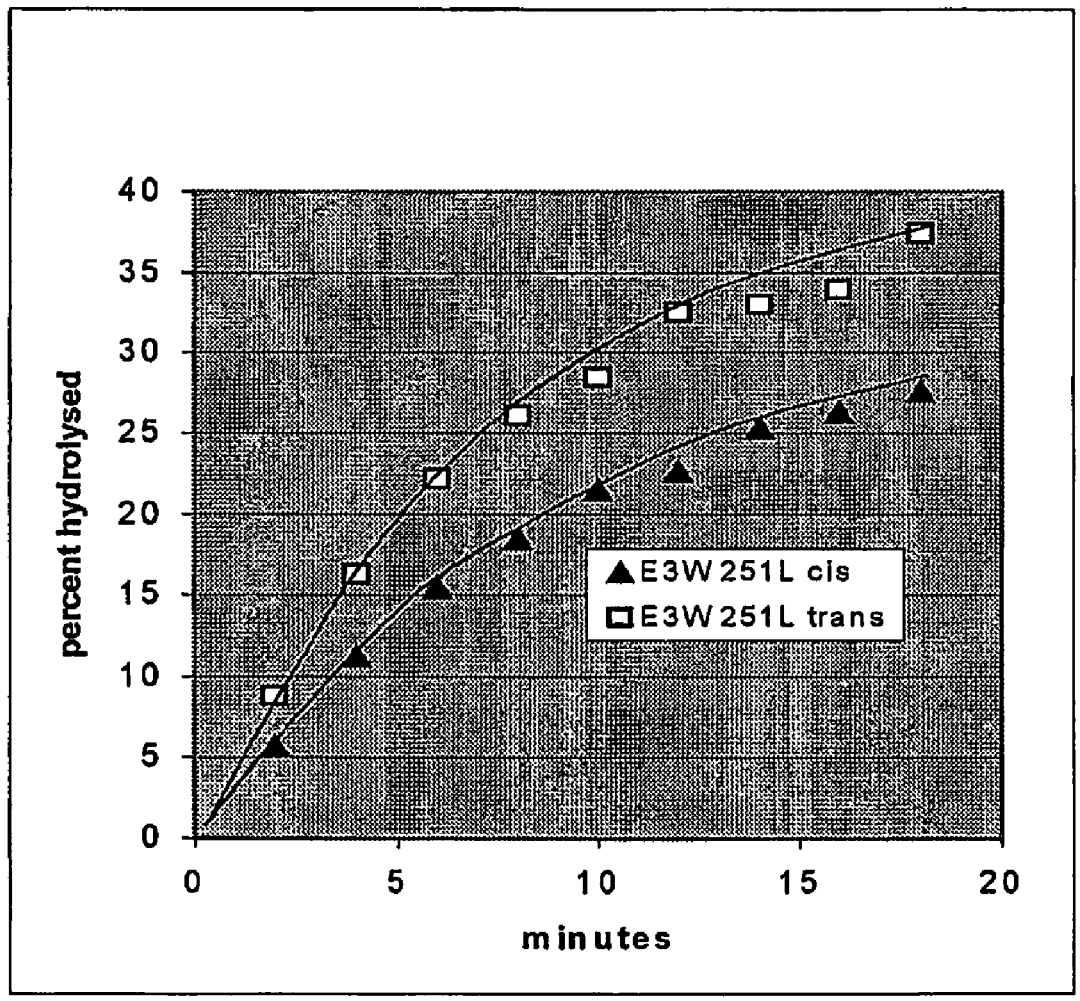

FIG. 5: Hydrolysis of cis and trans permethrin (0.5 μM by E3W251L.

KEY TO SEQUENCE LISTING

SEQ ID NO:1—Amino acid sequence of *Lucilia cuprina* E3 α-carboxylesterase.
SEQ ID NO:2—Amino acid sequence of *Drosophila melanogaster* EST23 α-carboxylesterase.
SEQ ID NO:3—Partial amino acid sequence of *Torpedo californica* acetylcholinesterase.

DETAILED DESCRIPTION OF THE INVENTION

General Techniques

Unless otherwise indicated, the recombinant DNA techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (Editors), Current Protocols in Molecular Biology, Greene Pub. Associates and Wiley-Interscience (1988, including all updates until present) and are incorporated herein by reference.

Pyrethroids

Pyrethroids are synthetic analogs of pyrethrum pesticides. For example, pyrethroids include (in each case common name in accordance with The Pesticide Manual, 12th Edition): permethrin, fenvalerate, esfenvalerate, cypermethrin, alpha-cypermethrin, deltamethrin, fenpropathrin, fluvalinate, flucythrinate, cyfluthrin, acrinathrin, tralomethrin, cyclopro-thrin, lambda-cyhalothrin, tefluthrin, bifenthrin, trans-fluthrin, zeta-cypermethrin, and halfenprox.

Type I pyrethroid compounds (e.g., permethrin) differ from type II pyrethroid compounds in that type II compounds possess a cyano group on the α-carbon atom of the phenoxybenzyl moiety. Some examples of type II pyrethroids are cypermethrin, deltamethrin, and fenvalerate.

Examples of pyrethroid pesticides which can be hydrolysed using the methods of the present invention include, but are not restricted to these compounds; 3-phenoxybenzyl(1RS)-cis, trans-3-(2,2-dichlorovinyl)-2,2-dimethylcyclopropane carboxylate [permethrin], α-cyano-3-phenoxybenzyl-1-(4-ethoxyphenyl)-2,2-dichlorocyclopropane carboxylate [cyloprothrin], (RS)-α-cyano-3-phenoxybenzyl(RS)-2-(4-chlorophenyl)-3-isovalerate [fenvalerate], (S)-α-cyano-3-phenoxybenzyl(S)-2-(4-chlorophenyl)isovalerate [esfenvalerate], α-cyano-3-phenoxybenzyl(S)-2-(4-difluoromethoxyphenyl) isovalerate [flucythrinate], α-cyano-3-phenoxybenzyl 2-(2-chloro-4-trifluoromethylaniline)isovalerate [fluvalinate], (RS)-α-cyano-3-phenoxybenzyl 2,2,3,3-tetramethylcyclopropane carboxylate [fenpropathrin], 3-phenoxybenzyl(1R)-cis, trans-chrysanthemate [d-fenothrin], (RS)-α-cyano-3-phenoxybenzyl(1R)-cis, trans-chrysanthemate [cyfenothrin], (RS)3-allyl-2-methyl-4-oxocyclopento-2-enyl(1RS)-cis, trans-chrysanthemate [allethrin], α-cyano-3-phenoxybenzyl(1R)-cis, trans-3-phenoxybenzyl (1R)-cis, trans-3-(2,2-dichlorovinyl)-2,2-dimethylcyclopropane carboxylate [cypermethrin], (S)-α-cyano-3-phenoxybenzyl(1R)-cis-3-(2,2-dibromovinyl)-2,2-dimethylcyclopropane carboxylate [deltamethrin], (S)-α-cyano-3-phenoxybenzyl(1R)-cis-2,2-dimethyl-3-(1,2,2,2-tetrabromoethyl)cyclopropane carboxylate [tralomethrin], 3,4,5,6-tetrahydroimidomethyl(1RS)-cis, trans-chrysanthemate [tetramethrin], 5-benzyl-3-furylmethyl(IRS)-cis, trans-chrysanthemate [resmethrin], α-cyano-4-fluoro-3-phenoxybenzyl(1R, trans)-2,2-dimethyl-3-(2,2-dichlorovinyl) cyclopropane carboxylate [cyfluthrin].

Polypeptides

By "substantially purified" we mean a polypeptide that has been separated from most of the lipids, nucleic acids, other polypeptides, and other contaminating molecules with which it is associated in its native state.

The % identity of a polypeptide is determined by GAP (Needleman and Wunsch, 1970) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. More preferably, the query sequence is at least 250 amino acids in length and the GAP analysis aligns the two sequences over a region of at least 250 amino acids. Even more preferably, the query sequence is at least 500 amino acids in length and the GAP analysis aligns the two sequences over a region of at least 500 amino acids.

As used herein, the term "mutant thereof" refers to mutants of a naturally occurring insect esterase which maintains at least some hydrolytic activity towards a hydrophobic ester pesticide or toxin when compared to the naturally occurring insect esterase from which they are derived. Preferably, the mutant has enhanced activity and/or altered stereospecificity when compared to the naturally occurring insect esterase from which they are derived.

Amino acid sequence mutants of naturally occurring insect esterases can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final protein product possesses the desired characteristics.

In designing amino acid sequence mutants, the location of the mutation site and the nature of the mutation will depend on characteristic(s) to be modified. In a particularly preferred embodiment, naturally occurring insect esterases are mutated to increase their ability to hydrolyse a hydrophobic ester pesticide or toxin, particularly a pyrethroid. The sites for mutation can be modified individually or in series, e.g., by (1) substituting first with conservative amino acid choices and then with more radical selections depending upon the results achieved, (2) deleting the target residue, or (3) inserting other residues adjacent to the located site. Examples of such mutants include; E3G137R, E3G137H, E3W251L, E3W251S, E3W251G, E3W251T, E3W251A, E3W251L/F309L, E3W251L/G137D, E3W251L/P250S, E3F309L, E3Y148F, E3E217M, E3F354W, E3F354L, and EST23W251L.

Mutants useful for the methods of the present invention can also be obtained by the use of the DNA shuffling technique (Patten et al., 1997). DNA shuffling is a process for recursive recombination and mutation, performed by random fragmentation of a pool of related genes, followed by reassembly of the fragments by primeness PCR. Generally, DNA shuffling provides a means for generating libraries of polynucleotides which can be selected or screened for, in this case, polynucleotides encoding enzymes which can hydrolyse a hydrophobic ester pesticide or toxin. The stereospecificity of the selected enzymes can also be screened.

Amino acid sequence deletions generally range from about 1 to 30 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active or binding site(s). Other sites of interest are those in which particular residues obtained from various strains or species are identical. These positions may be important for biological activity. These sites, especially those falling within a sequence of at least three other identically conserved sites, can be substituted in a relatively conservative manner. Such conservative substitutions are shown in Table 1 under the heading of "exemplary substitutions".

Furthermore, if desired, unnatural amino acids or chemical amino acid analogues can be introduced as a substitution or addition into the insect esterase, or mutants thereof. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are insect esterases, or mutants thereof, which are differentially modified during or after synthesis, e.g., by biotinylation, benzylation, glycosylation, acetylation, phosphorylation, derivatization by known protecting/blocking groups, proteolytic cleavage, linkage to an antibody molecule or other cellular ligand, etc. These modifications may serve to increase the stability and/or bioactivity of the polypeptide of the invention.

TABLE 1

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Insect esterases, and mutants thereof, can be produced in a variety of ways, including production and recovery of natural proteins, production and recovery of recombinant proteins, and chemical synthesis of the proteins. In one embodiment, an isolated polypeptide encoding the insect esterase, or mutant thereof, is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells producing the insect esterase, or mutant thereof, can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Polynucleotides

By "isolated polynucleotide", we mean a polynucleotide separated from the polynucleotide sequences with which it is associated or linked in its native state. Furthermore, the term "polynucleotide" is used interchangeably herein with the term "nucleic acid molecule".

The % identity of a polynucleotide is determined by GAP (Needleman and Wunsch, 1970) analysis (GCG program) with a gap creation penalty=5, and a gap extension penalty=0.3. The query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides.

Recombinant Vectors

Recombinant vectors can be used to express an insect esterase, or mutant thereof, for use in the methods of the present invention. In addition, in another embodiment of the present invention includes a recombinant vector, which includes at least one isolated polynucleotide molecule of the present invention, inserted into any vector capable of delivering the polynucleotide molecule into a host cell. Such vectors contain heterologous polynucleotide sequences, that is polynucleotide sequences that are not naturally found adjacent to polynucleotide encoding the insect esterase, or mutant thereof, and that preferably are derived from a species other than the species from which the esterase is derived. The vector can be either RNA or DNA, either prokaryotic or eukaryotic, and typically is a virus or a plasmid.

One type of recombinant vector comprises a polynucleotide encoding an insect esterase, or mutant thereof, operatively linked to an expression vector. The phrase operatively linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, other animal, and plant cells. Preferred expression vectors of the present invention can direct gene expression in bacterial, yeast, arthropod and mammalian cells and more preferably in the cell types disclosed herein.

Expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, expression vectors which comprise a polynucleotide encoding an insect esterase, or mutant thereof, include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, arthropod and mammalian cells, such as, but not limited to, tac, lac, trp, trc, oxy-pro, omp/lpp, rrnB, bacteriophage lambda, bacteriophage T7, T7lac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers.

Polynucleotide encoding an insect esterase, or mutant thereof, may also (a) contain secretory signals (i.e., signal segment nucleic acid sequences) to enable an expressed insect esterase, or mutant thereof, to be secreted from the cell that produces the polypeptide and/or (b) contain fusion sequences. Examples of suitable signal segments include any signal segment capable of directing the secretion of an insect esterase, or mutant thereof. Preferred signal segments include, but are not limited to, tissue plasminogen activator (t-PA), interferon, interleukin, growth hormone, histocompatibility and viral envelope glycoprotein signal segments, as well as natural signal sequences. In addition, polynucleotides encoding an insect esterase, or mutant thereof, can be joined to a fusion segment that directs the encoded protein to the proteosome, such as a ubiquitin fusion segment.

Host Cells

Another embodiment of the present invention includes a recombinant cell comprising a host cell transformed with one or more polynucleotides encoding an insect esterase, or mutant thereof. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism A transformed polynucleotide encoding an insect esterase, or mutant thereof, can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide encoding an insect esterase, or mutant thereof. Host cells of the present invention either can be endogenously (i.e., naturally) capable of producing an insect esterase or mutant thereof, or can be capable of producing such proteins after being transformed with at least one polynucleotide encoding an insect esterase, or mutant thereof. Host cells of the present invention can be any cell capable of producing at least one insect esterase, or mutant thereof, and include bacterial, fungal (including yeast), parasite, arthropod, animal and plant cells. Preferred host cells include bacterial, mycobacterial, yeast, arthropod and mammalian cells. More preferred host cells include *Salmonella, Escherichia, Bacillus, Listeria, Saccharomyces, Spodoptera, Mycobacteria, Trichoplusia*, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *E. coli*, including *E. coli* K-12 derivatives; *Salmonella typhi; Salmonella typhimurium*, including attenuated strains; *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK cells and/or HeLa cells.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of a polynucleotide encoding an insect esterase, or mutant thereof, include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

Compositions

Compositions useful for the methods of the present invention, or which comprise a polypeptide of the present invention, include excipients, also referred to herein as "acceptable carriers". An excipient can be any material that the animal, plant, plant or animal material, or environment (including soil and water samples) to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal or o-cresol, formalin and benzyl alcohol. Excipients can also be used to increase the half-life of a composition, for example, but are not limited to, polymeric controlled release vehicles, biodegradable implants, liposomes, bacteria, viruses, other cells, oils, esters, and glycols.

Furthermore, the insect esterase, or mutant thereof, can be provided in a composition which enhances the rate and/or degree of degradation of hydrophobic ester pesticides or toxins, or increases the stability of the polypeptide. For example, the insect esterase, or mutant thereof, can be immobilized on a polyurethane matrix (Gordon et al., 1999), or encapsulated in appropriate liposomes (Petrikovics et al. 2000a and b). The insect esterase, or mutant thereof, can also be incorporated into a composition comprising a foam such as those used routinely in fire-fighting (Lejeune et al., 1998).

As would be appreciated by the skilled addressee, the insect esterase, or mutant thereof, could readily be used in a sponge or foam as disclosed in WO 00/64539, the contents of which are incorporated herein in their entirety.

One embodiment of the present invention is a controlled release formulation that is capable of slowly releasing a composition comprising an insect esterase, or mutant thereof, into an animal, plant, animal or plant material, or the environment (including soil and water samples). As used herein, a controlled release formulation comprises an insect esterase, or mutant thereof, in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphere, and transdermal delivery systems. Preferred controlled release formulations are biodegradable (i.e., bioerodible).

A preferred controlled release formulation of the present invention is capable of releasing an insect esterase, or mutant thereof, into soil or water which is in an area sprayed with a hydrophobic ester pesticide or toxin. The formulation is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

The concentration of the insect esterase, or mutant thereof, (or host cell expressing the insect esterase, or mutant thereof) that will be required to produce effective compositions for degrading a hydrophobic ester pesticide or toxin will depend on the nature of the sample to be decontaminated, the concentration of the hydrophobic ester pesticide or toxin in the sample, and the formulation of the composition. The effective concentration of the insect esterase, or mutant thereof, (or host cell expressing the insect esterase, or mutant thereof) within a composition can readily be determined experimentally, as will be understood by the skilled artisan.

Surfactants

It is envisaged that the use of a surfactant in the method of the present invention may liberate hydrophobic ester pesticides and/or toxins, from any, for example, sediment in the sample. Thus increasing efficiency of the method of the present invention.

Surfactants are amphipathic molecules with both hydrophilic and hydrophobic (generally hydrocarbon) moieties that partition preferentially at the interface between fluid phases and different degrees of polarity and hydrogen bonding such as oil/water or air/water interfaces. These properties render surfactants capable of reducing surface and interfacial tension and forming microemulsion where hydrocarbons can solubilize in water or where water can solubilize in hydrocarbons. Surfactants have a number of useful properties, including dispersing traits.

Biosurfactants are a structurally diverse group of surface-active molecules synthesized by microorganisms. These molecules reduce surface and interfacial tensions in both aqueous solutions and hydrocarbon mixtures. Biosurfactants have several advantages over chemical surfactants, such as lower toxicity, higher biodegradability, better environmental compatability, higher foaming, high selectivity and specificity at extreme temperatures, pH and salinity, and the ability to be synthesized from a renewable source.

Biosurfactants useful in the bioremediation methods of the present invention include, but are not limited to; glycolipids such as rhamnolipids (from, for example, *Pseudomonas aeruginosa*), trehalolipids (from, for example, *Rhodococcus ethropolis*), sophorolipids (from, for example, *Torulopsis bombicola*), and cellobiolipids (from, for example, *Ustilago zeae*); lipopeptides and lipoproteins such as serrawettin (from, for example, *Serratia marcescens*), surfactin (from, for example, *Bacillus subtilis*); subtilisin (from, for example, *Bacillus subtilis*), gramicidins (from, for example, *Bacillus brevis*), and polymyxins (from, for example, *Bacillus polymyxa*); fatty acids, neutral lipids, and phospholipids; polymeric surfactants such as emulsan (from, for example, *Acinetobacter calcoaceticus*), biodispersan (from, for example, *Acinetobacter calcoaceticus*), mannan-lipid-protein (from, for example, *Candida tropicalis*), liposan (from, for example, *Candida lypolytica*), protein PA (from, for example, *Pseudomonas aeruginosa*); and particulate biosurfactants such as vesicles and fimbriae from, for example, *A. calcoaceticus*.

Transgenic Plants

The term "plant" refers to whole plants, plant organs (e.g. leaves, stems roots, etc), seeds, plant cells and the like. Plants contemplated for use in the practice of the present invention include both monocotyledons and dicotyledons. Exemplary monocotyledons include wheat, barley, rye, triticale, oats, rice, and the like.

Transgenic plants, as defined in the context of the present invention include plants (as well as parts and cells of said plants) and their progeny which have been genetically modified using recombinant DNA techniques to either i) cause the production of an the insect esterase, or mutant thereof, in the desired plant or plant organ.

Several techniques exist for introducing foreign genetic material into a plant cell. Such techniques include acceleration of genetic material coated onto microparticles directly into cells (see, for example, U.S. Pat. Nos. 4,945,050 and 5,141,131). Plants may be transformed using *Agrobactelium* technology (see, for example, U.S. Pat. Nos. 5,177,010, 5,104,310, 5,004,863, 5,159,135). Electroporation technology has also been used to transform plants (see, for example, WO 87/06614, U.S. Pat. Nos. 5,472,869, 5,384,253, WO 92/09696 and WO 93/21335). In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during development and/or differentiation using appropriate techniques described herein.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of plant promoters include, but are not limited to ribulose-1,6-bisphosphate carboxylase small subunit, beta-conglycinin promoter, phaseolin promoter, ADH promoter, heat-shock promoters and tissue specific promoters. Promoters may also contain certain enhancer sequence elements that may improve the transcription efficiency. Typical enhancers include but are not limited to Adh-intron 1 and Adh-intron 6.

Constitutive promoters direct continuous gene expression in all cells types and at all times (e.g., actin, ubiquitin, CaMV 35S). Tissue specific promoters are responsible for gene expression in specific cell or tissue types, such as the leaves or seeds (e.g., zein, oleosin, napin, ACP, globulin and the like) and these promoters may also be used. Promoters may also be active during a certain stage of the plants' development as well as active in plant tissues and organs. Examples of such promoters include but are not limited to pollen-specific, embryo specific, corn silk specific, cotton fiber specific, root specific, seed endosperm specific promoters and the like.

Under certain circumstances it may be desirable to use an inducible promoter. An inducible promoter is responsible for expression of genes in response to a specific signal, such as: physical stimulus (heat shock genes); light (RUBP carboxylase); hormone (Em); metabolites; and stress. Other desirable transcription and translation elements that function in plants may be used.

In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the cauliflower mosaic virus (35S and 19S) and the like may be used.

The following examples are offered for illustration purposes, and are not intended to limit or define the invention in any manner.

EXAMPLES

Example 1

Construction of Mutants

An alignment of the amino acid sequence of the E3 enzyme with that of a vertebrate acetylcholinesterase (TcAChE, for which the three dimensional structure is known; Sussman et al., 1991) is given in FIG. 1. Mutants of E3 and EST23 were constructed using the QuickChange™ Site-Directed Mutagenesis Kit of Stratagene and are named according to the number of the residue that has been changed, and the nature of that change. For example, mutant E3W251L is an E3 mutant in which the Trp residue at position 251 in the wild-type enzyme (i.e. E3WT) has been mutated to Leu.

E3 and EST23 enzymes were expressed using the baculovirus expression system as described by Newcomb et al. (1997), but using the HyQ SFX-insect serum-free medium (HyClone) for increased expression. Cell extracts were prepared by lysing the cells at a concentration of $10^8$ cells $ml^{-1}$ in 0.1M phosphate buffer pH 7.0 containing 0.05% Triton X-100. Extracts were then titrated for the number of esterase molecules using a fluorometric assay based on the initial release of coumarin (a fluorescent compound) upon phosphorylation of the enzyme by diethylcoumaryl phosphate (dECP).

FIG. 2 illustrates the proposed configuration of the active site of E3 (based on the three dimensional structure of vertebrate AChE) in an acylation reaction. We have examined mutations in seven E3 residues in regions corresponding to three distinct subsites of the known ACHE active site. These are the oxyanion hole (E3 residue 137), the anionic site (E3 residues 148, 217 and 354) and acyl binding pocket (E3 residues 250, 251 and 309). The anionic site and acyl binding pocket correspond to the p1 and p2 subsites in the nomenclature of Jarv (1984).

Mutations in the Oxyanion Hole

In TcAChE the oxyanion hole comprises Gly118, Gly119 and Ala201, which corresponds to Gly136, Gly137 and Ala219 in E3. These residues are highly conserved throughout the carboxyl/cholinesterase multigene family (Oakeshott et al., 1999) and there is empirical evidence for the conservation of the oxyanion hole structure from X-ray crystallographic studies of several cholinesterases and lipases (Cygler and Schrag, 1997), albeit the structure does change during interfacial activation in some lipases (Derewenda et al., 1992). There is also empirical structural evidence for their function in stabilising the oxyanion formed by the carbonyl oxygen of the carboxylester substrate as the first transition state during catalysis (Grochulski et al., 1993; Martinez et al., 1994). This stabilisation is achieved by a network of hydrogen bonds to the amide groups of the three key residues in the peptide chain (Ordentlich et al., 1998). Recently Koellner et al. (2000) have also shown that both Gly residues in the ACHE oxyanion hole make hydrogen bonds with buried "structural" water molecules, which are retained during catalysis and thought to act as lubricants to facilitate traffic of substrates and products within the active site.

Three further mutations were made to the Gly137 of E3 in addition to the G137D found naturally in OP resistant *L. cuprina*. First, Glu was substituted as the other acidic amino acid, in G137E. The mutant G137H was also constructed, because His is also non-protonated at neutral pH ($pK_a$ about 6.5 cf 4.4 for Asp and Glu) and it was found to confer some OP hydrolysis on human butyrylcholinesterase when substituted for either Gly in its oxyanion hole (Broomfield et al., 1999). Finally, Arg ($pK_a$ around 12) was substituted at position 137, to examine the effects of the most strongly basic substitution possible.

Mutations in the Acyl Binding Pocket

The acyl binding pockets of structurally characterised cholinesterases are formed principally from four non-polar residues, three of which are generally also aromatic. Together they create a strongly hydrophobic pocket to accommodate the acyl moiety of bound substrate. The four residues in TcAChE are Trp233, Phe288, Phe290 and Val400 corresponding to Trp251, Val307, Phe309 and Phe422 in E3. Similar arrays of hydrophobic residues appear to be conserved at the corresponding sites of most carboxyl/cholinesterases (Oakeshott et al., 1993; Robin et al., 1996; Yao et al., 1997; Harel et al., 2000). In particular Trp is strongly conserved at residue 233/251 and 290/309 is Phe in cholinesterases and most carboxylesterases, albeit a Leu or Ile in several lipases and a few carboxylesterases. The residue corresponding to TcAChE Phe288 is typically a branched chain aliphatic amino acid in cholinesterases that show a preference for longer chain esters such as butyrylcholine. This includes mammalian butyrylcholinesterase and some insect acetylcholinesterases, which have a butyrylcholinesterase-like substrate specificity. The branched chain aliphatic amino acid appears to provide a greater space in the acyl-binding pocket to accommodate the larger acyl group.

Mutational studies of 288/307 and 290/309 in several cholinesterases confirm their key role in determining aspects of substrate specificities related to acyl group identity. In human AChE replacement of the Phe at either position with a smaller residue like Ala improves the kinetics of the enzyme for substrates like propyl- or butyl-(thio)choline with larger acyl groups than the natural acetyl (thio)choline substrate (Ordentlich et al., 1993). In AChE from *D. melanogaster* and the housefly, *Musca domestica*, natural mutations of their 290/309 equivalent to the bulkier, polar Tyr that contributes to target site OP resistance have lower reactivity to both acetylcholine and OPs (Fournier et al., 1992; Walsh et al., 2001). For *D. melanogaster* AChE, substitution of this Phe residue with the smaller Leu gave the predicted increase in OP sensitivity, although surprisingly replacement with other small residues like Gly, Ser or Val did not (Villatte et al., 2000).

Trp 233/251 has received much less attention in mutational studies of cholinesterases but our prior work on E3 shows its replacement with a smaller Leu residue again increases reactivity for carboxylester substrates with bulky acyl moieties as in malathion, or for OPs (Campbell et al., 1998a, b; Devonshire et al., 2002). A mutation to Gly has also been found in a homologue from the wasp, *Anisopteromalus calandrae*, that shows enhanced malathion carboxylesterase (MCE) kinetics (Zhu et al., 1999) while a Ser has been found in a homologue from *M. domestica* that may be associated with malathion resistance (Claudianos et al., 2002). In respect of OP hydrolase activity Devonshire et al. (2002) proposed that the particular benefit of such mutations is to accommodate the inversion about the phosphorus that must occur for the second hydrolysis stage of the reaction to proceed. Notably Devonshire et al. (2002) found that the $k_{cat}$ for OP hydrolase activity of E3W251L is an order of magnitude higher for dMUP, with its smaller dimethyl phosphate group than for dECP, which has a diethyl phosphate group. This suggests that there remain tight steric constraints on the inversion even in a mutant with a larger acyl pocket.

We have mutated both the W251 and F309 residues of E3 as well as the P250 immediately adjacent to W251. In addition to the previously characterised natural W251L mutation we have now analysed substitutions with four other small amino acids in W251S, W251G, W251T and W251A. A double mutant of W251L and P250S was also analysed, because a natural variant of the ortholog of E3 in *M. domestica* with high MCE activity has Ser and Leu at positions 250 and 251, respectively. Only one F309 substitution was examined, F309L, which the AChE results suggest should enhance MCE and OP hydrolyse activities. F309L was analysed alone and as a double mutant with W251L.

Mutations in the Anionic Site

The anionic site of cholinesterases is sometimes called the quaternary binding site (for the quaternary ammonium in acetylcholine), or the p1 subsite in the original nomenclature of Jarv (1984). It principally involves Trp 84, Glu 199 and Phe 330, with Phe 331 and Tyr 130 (TcAChE nomenclature) also involved. Except for Glu 199 it is thus a highly hydrophobic site. Glu 199 is immediately adjacent to the catalytic Ser 200. The key residues are highly conserved across cholinesterases and to a lesser extent, many carboxylesterases (Oakeshott et al., 1993; Ordentlich et al., 1995; Robin et al., 1996; Claudianos et al., 2002). Except for Trp 84 (the sequence alignment in FIG. 1 shows that E3 is missing residues corresponding to AChE residues 74-85), E3 has identical residues to TcAChE at the corresponding positions (217, 354 and 148, respectively). Interestingly the equivalent of Glu 199 is Gln and the equivalent of the Phe 330 is Leu in some lipases and certain carboxylesterases, whose substrates are known to have small leaving groups (Thomas et al., 1999; Campbell et al., 2001; Claudianos et al., 2002).

Structural and mutational studies have provided a detailed picture of the role of the anionic site in cholinesterase catalysis. The key residues form part of a hydrogen bonded network at the bottom of the active site, with Tyr 130 and Glu 199 also sharing contact with a structural water molecule (Ordentlich et al., 1995; Koellner et al., 2000). The anionic site undergoes a conformational change when substrate binds a peripheral binding site at the lip of the active site gorge, the new conformation accommodating the choline (leaving) group of the substrate and facilitating the interaction of its carbonyl carbon with the catalytic Ser 200 (Shafferman et al., 1992; Ordentlich et al., 1995; 1996). Consequently the site functions mainly in the first, enzyme acylation, stage of the reaction and, in particular, in the formation of the non-covalent transition state (Nair et al., 1994). Therefore mutations of the key residues mainly affect $K_m$ rather than $k_{cat}$. The interactions with the choline leaving group are mainly mediated through non-polar and π-electron interactions, principally involving Trp 84 and Phe 330 (Ordentlich et al., 1995).

Studies with OP inhibitors suggest that the anionic site of cholinesterases also accommodates their leaving group but there is some evidence that part of the site (mainly Glu 199 and Tyr 130; also possibly Ser 226) may also then affect the reactivity of the phosphorylated enzyme (Qian and Kovach, 1993; and see also Ordentlich et al., 1996; Thomas et al., 1999).

There has been little mutational analysis of carboxylesterase sites corresponding to the AChE anionic site but one interesting exception involves the EST6 carboxylesterase of *D. melanogaster*, which has a His at the equivalent of Glu 199. A mutant in which this His is replaced by Glu shows reduced activity against various carboxylester substrates but has acquired some acetylthiocholine hydrolytic activity (Myers et al., 1993). The E4 carboxylesterase of the aphid, *Myzus persicae*, has a Met at this position and this enzyme is unusually reactive to OPs (Devonshire and Moores, 1982). However, it is not known whether the Met contributes to the OP hydrolase activity. Similarly, a Y148F substitution is one of several recorded in the E3 ortholog in an OP resistant strain (ie also G137D) of *M. domestica* but it is not known whether this change directly contributes to OP hydrolase activity (Claudianos et al., 1999).

The Y148, E217 and F354 residues in E3 have now been mutated. E217M and Y148F mutations were made to test whether the corresponding mutations in the *M. persicae* and *M. domestica* enzymes above contribute directly to their OP reactivity. Y148F is also tested in a G137D double mutant since this is the combination found in the resistant *M. domestica*. F354 was mutated both to a smaller Leu residue and a larger Trp, Leu commonly being found at this position in lipases (see above).

Example 2

Enzyme Titrations

Four 100 µl reactions were set up for each expressed esterase in microplate columns 1-4:
plate well blank containing 0.025% Triton X-100, 0.1M phosphate buffer pH 7.0;
substrate blank containing 100 µM dECP in 0.025% Triton X-100, 0.1M phosphate buffer pH 7.0;
cell blank containing 50 µl cell extract mixed 1:1 with 0.1M phosphate buffer pH 7.0;
titration reaction containing 50 µl cell extract mixed 1:1 with 0.1M phosphate buffer pH 7.0 containing 200 µM dECP.

All components except dECP (freshly prepared at a concentration of 200 µM in buffer) were placed in the wells. Several enzymes were assayed simultaneously in a plate, and the reactions were started by adding dECP simultaneously to the 2nd and 4th wells down a column. The interval to the first reading (typically 1 minute) was noted for the subsequent calculations.

The mean value for the plate well blank (A) was subtracted from all readings before further calculations. Preliminary experiments with various cell extracts showed that they gave some fluorescence at 460 nm and that their addition to solutions of the assay product, 7-hydroxycoumarin, quenched fluorescence by 39(±7)%. Fluorescence values in the titration reactions (D) were therefore corrected for this quenching effect after subtraction of the intrinsic fluorescence of the cell extracts (C). Finally, the substrate blank (B), taken as the mean from all the simultaneous assays in a plate, was subtracted to give the corrected fluorescence caused by the esterase-released coumarin. These corrections were most important for cell lines expressing esterase at very low level (<1 pmol/µl extract).

The fully corrected data were plotted as a progress curve, and the equilibrium slope extrapolated back to zero time to determine the amount of esterase, based on its stoichiometric interaction with the inhibitor (the 100 µM concentration of dECP gave full saturation of the esterase catalytic sites of all these enzymes in 10-20 minutes). A calibration curve for 7-hydroxycoumarin was prepared alongside the reactions in all plates, and used to calculate molar concentration of enzyme and product formation.

FIG. 3 shows the results of representative titration experiments performed on cell extracts containing baculovirus expressed esterases.

Example 3

Permethrin Hydrolysis Assays

Expressed enzymes were tested for permethrin hydrolytic activity using a radiometric partition assay for acid-labelled compounds, or a TLC based assay for those labelled in the alcohol moiety (Devonshire and Moores, 1982). Features of the assays include keeping the concentration of permethrin below its published solubility in aqueous solution (0.5 µM, the concentration of detergent (used to extract the enzyme from the insect cells in which it is expressed) below the critical micelle concentration (0.02% for Triton X100), and performing the assays quickly (ie within 10-30 minutes) to minimise the substrate sticking to the walls of the assay tubes (glass tubes were used to minimise stickiness). At these permethrin concentrations the enzyme is not saturated by the substrate, so $K_m$ values could not be determined. However, specificity constants ($k_{cat}/K_m$) could be calculated accurately for each of the enzymes with permethrin activity, which allows direct comparison of their efficiency at low substrate concentrations. The power of the analyses was increased by separating permethrin into its cis and trans isomers.

(a) Separation of cis and trans Isomers of Permethrin

Commercial preparations of permethrin contain four stereoisomers: 1S cis, 1R cis, 1S trans, 1R trans (FIG. 4). Preparative thin layer chromatography (TLC) on silica was used to separate the isomers into two enantiomer pairs: 1S/1R cis and 1S/1R trans. The enantiomers could not be separated further. Enzyme preparations could then be assayed for the hydrolysis of each enantiomer pair.

(b) Assay Protocol

Pyrethroids Radiolabelled in the Acid Moiety

This assay (Devonshire and Moores, 1982) is used for permethrin isomers. It relies on incubating the expressed esterase with radiolabelled substrate and then measuring the radioactive cyclopropanecarboxylate anion in the aqueous phase after extracting the unchanged substrate into organic solvent. Based on previous experience, the best extraction protocol utilises a 2:1 (by volume) mixture of methanol and chloroform. When mixed in the appropriate proportion with aliquots of the assay incubation, the consequent mixture of buffer, methanol and chloroform is monophasic, which serves the purpose of stopping the enzyme reaction and ensuring the complete solubilization of the pyrethroid. Subsequent addition of an excess of chloroform and buffer exceeds the capacity of the methanol to hold the phases together, so that the organic phase can be removed and the product measured in the aqueous phase. In detail, the protocol is as follows.

Phosphate buffer (0.1M, pH 7.0) was added to radiolabelled permethrin (50 μM in acetone) to give a 1 μM solution and the assay then started by adding an equal volume of expressed esterase appropriately diluted in the same buffer. Preliminary work had established that the concentration of detergent (Triton X-100 used to extract esterase from the harvested cells) in the incubation had to be below its CMC (critical micelle concentration of 0.02%) to avoid the very lipophilic pyrethroid partitioning into the micelles and becoming unavailable to the enzyme. Typically, the final volume of the assay was 500-1000 μl, with substrate and acetone concentrations 0.5 μM and 1%, respectively. At intervals ranging from 30 seconds to 10 minutes at a temperature of 30°, 100 μl aliquots of the incubation were removed, added to tubes containing 300 μl of the 2:1 methanol chloroform mixture and vortex-mixed. The tubes were then held at room temperature until a batch could be further processed together, either at the end of the incubation or during an extended sampling interval. After adding 50 μl buffer and 100 μl chloroform, the mixture was vortex-mixed, centrifuged and the lower organic phase removed with a 500 μl Hamilton syringe and discarded. The extraction was repeated after adding a further 100 μl chloroform, and then 200 μl of the upper aqueous phase was removed (using a pipettor with a fine tip) for scintillation counting. It is critical to avoid taking any of the organic phase. Since the final volume of the aqueous phase was 260 μl (including some methanol), the total counts produced in the initial 100 μl aliquot were corrected accordingly.

Pyrethroids Radiolabelled in the Alcohol Moiety i) Type I Pyrethroids—Dibromo Analogues (NRDC157) of Permethrin:

The 3-phenoxybenzyl alcohol formed on hydrolysis of these esters does not partition into the aqueous phase in the chloroform methanol extraction procedure. It was therefore necessary to separate this product from the substrate by TLC on silica (Devonshire and Mooers, 1982). In detail, the protocol is as follows.

Incubations were set up as for the acid-labelled substrates. The reactions were stopped at intervals in 100 μl aliquots taken from the incubation by immediately mixing with 200 acetone at −79° (solid $CO_2$). Then 100 μl of the mixture was transferred, together with 3 μl non-radioactive 3-phenoxybenzyl alcohol (2% in acetone), on to the loading zone of LinearQ channelled silica F254 plates (Whatman). After developing in a 10:3 mixture of toluene (saturated with formic acid) with diethyl ether, the substrate and product were located by radio- autography for 6-7 days (confirming an identical mobility of the product to the cold standard 3-phenoxbenzyl alcohol revealed under UV light). These areas of the TLC plate were then impregnated with Neatan (Merck) and dried, after which they were peeled from the glass support and transferred to vials for scintillation counting. The counts were corrected for the 3-fold dilution of the initial 100 μl by acetone before spotting on the silica.

ii) Type II Pyrethroids—Deltamethrin Isomers:

Preliminary experiments, in which incubations were analysed by TLC as above, showed primarily the formation of 3-phenoxbenzoic acid, in line with literature reports that the initial cyanohydrin hydrolyis product is rapidly converted non-enzymically to the acid. Since the TLC assay is more protracted than the chloroform-methanol extraction procedure, the latter (as described above for acid-labelled pyrethroids) was adopted to measure the 3-phenoxbenzoate anion produced from these substrates.

For all assays the molar amount of product formed was calculated from the known specific activity of the radiolabelled substrate. Early experiments on the expressed E3WT esterase showed that the rate of hydrolysis was directly proportional to the concentration of 1RS cis or 1RS trans permethrin in the assay up to 0.5 μM, i.e. there was no accumulation of Michaelis complex. Assays at concentrations greater than 0.5 μM, which approximates the published aqueous solubility of permethrin, gave erratic results so precluding the measurement of $K_m$ and $k_{cat}$. Furthermore, with the racemic substrates, the rate of hydrolysis slowed dramatically once approximately 50% of the substrate had been hydrolysed, indicating that only one of the two enantiomers (1R or 1S present in equal amounts in a racemic mixture) was readily hydrolysed, in line with previously published data for an esterase from aphids (Devonshire and Moores, 1982). Assay conditions were therefore adjusted to measure the hydrolysis of the more-readily hydrolysed enantiomer in each pair. Sequential incubation of trans permethrin with E3WT homogenates confirmed that both showed preference for the 1S trans enantiomer. In all cases, the rate of hydrolysis at 0.5 μM (or 0.25 μM for the one enantiomer in racemic substrates), together with the molar amount of esterase determined by titration with dECP, were used to calculate the specificity constant ($k_{cat}/K_m$) since it was not possible to separate these kinetic parameters. The same considerations about substrate solubility and proportionality of response to its concentration were assumed for all enzymes and substrates.

(c) Calculation of Specificity Constants

FIG. 5 presents the results of an experiment in which the trans- and cis-isomers of permethrin were hydrolysed by the E3W251L enzyme.

Since the rate of hydrolysis of permethrin isomers was directly proportional to the concentration of substrate used up to 0.5 μM (i.e. there was no significant formation of Michaelis complex), it was not possible to measure $K_m$ and $k_{cat}$ as independent paramters. At concentrations well below the $K_m$, the Michaelis-Menten equation simplifies to:

$$v = \frac{k_{cat}}{K_m}[S][E]$$

The specificity constant (ie $k_{cat}/K_m$) can therefore be calculated from the above equation using the initial hydrolysis rate (pmol/min, calculated from the known specific activity of the radiolabelled substrate) and the concentrations of substrate and enzyme in the assay. The diffusion-limited maximum value for a specificity constant is $10^8$-$10^9$ M$^{-1}$sec$^{-1}$ (Stryer, 1981).

Example 4

Malathion Hydrolysis Assays

MCE activity was assayed as described by Campbell et al. (1998), but without diluting the specific activity of the $^{14}$C malathion (25mCi mmol$^{-1}$) for enzymes that appeared to have a low $K_m$. This was an end-point assay in which malathion was extracted into an organic phase while radiolabelled malathion carboxylic acids, the hydrolysis products remained, in the aqueous phase. Activity was measured over the range 50 nM to 1 µM to determine the $K_m$ and $k_{cat}$, and analysed by non-linear regression using the Enzfitter 1.05 software (Elsevier-Biosoft), with graphical output to reveal any deviation from Michaelis-Menten kinetics. Specificity constants were calculated directly from the $K_m$ and $k_{cat}$, values.

Example 5

Permethrin Hydrolytic Activity of E3 and EST23 Variants

Table 2 summarises the kinetic data obtained for eighteen E3 and three EST23 variants using cis- and trans-permethrin as substrates. The malathion hydrolytic activity of the enzymes is also given for comparison. In each case the data represent the hydrolysis of the enantiomer that is hydrolysed the fastest out of each of the 1S/1R cis and 1S/1R trans isomer pairs (see above).

The E3WT enzyme found in OP susceptible blowflies, and its EST23 *D. melanogaster* orthologue, showed significant levels of permethrin hydrolytic activity, which was specific for the trans isomers. The wild-type enzymes showed at least an order of magnitude higher activity for malathion (although this high MCE activity does not confer malathion resistance on the blowfly because the enzyme is readily inhibited by the malaoxon produced in vivo by the fly; Campbell et al., 1998). Mutations in either the acyl binding pocket or anionic site regions of the active site of the E3 enzyme resulted in significant increases in activity for both the trans and cis isomers of permethrin. These increases in permethrin hydrolysis were not in the main correlated with increases in malathion hydrolytic activity.

a) Oxyanion Hole Mutations

The E3G137D mutation is responsible for diazinon resistance in the sheep blowfly. In this mutant the very small, aliphatic, neutral Gly residue in the oxyanion hole region of the active site of the enzyme is replaced by an acidic Asp, allowing hydrolysis of a bound oxon OP molecule. However, this mutant (and its *D. melanogaster* orthologue) had reduced activity for trans-permethrin in particular, compared to that of the wild-type enzyme. This activity was not increased by substitution of Gly-137 with either His or Glu. However, substitution of Gly-137 with Arg did not affect the activity for either cis- or trans-permethrin appreciably. The linear nature of Arg might mean that it can fold easily and not interfere with binding of permethrin to the active site. The MCE activity of this group of mutants correlated broadly with their activity for trans permethrin in particular, indicating effects of G137 substitutions on the accommodation and stabilisation of the substrate acyl group. Effects are generally smaller for permethrin than malathion but this is consistent with the somewhat smaller acyl group for permethrin.

b) Acyl Binding Pocket Mutations

The E3W251L mutation, which replaces the large aromatic Trp reside with the smaller aliphatic Leu in the acyl pocket of the active site, resulted in a 7-fold increase in trans-permethrin hydrolysis and the acquisition of substantial cis-permethrin hydrolysis. This is the mutation responsible for the acquisition of malathion resistance in the sheep blowfly. The MCE activity of this mutant was 2-fold higher than that of the wild-type enzyme. The effect of W251L in EST23 was essentially the same as for E3. Replacement of Trp-251 with even smaller residues in E3 (Thr, Ser, Ala and Gly in decreasing order of size) also resulted in an increase in permethrin hydrolytic activity, although the activity of these mutants was not as high as that of E3W251L. Clearly, steric factors are not the only consideration in the activity of the mutants. For example, Thr and Ser both contain hydroxyl groups and are hydrophilic. Furthermore, Ala is both aliphatic and hydrophobic (like Leu) and even smaller than Leu, yet this mutant was as active for permethrin as the W251L mutant. Opening up the oxyanion hole of the W251L mutant (ie E3P250S/W251L) also decreased its activity for both cis- and trans-permethrin, although the activity was still higher than that of the wild type. It is interesting to note that increases in specificity constants for permethrin for all W251 mutants in E3 as well as W251L in EST23 compared to those of the wild types were uniformly more pronounced for the cis isomers. Whereas the wild type enzymes yielded trans:cis ratios of at least 20:1, these ratios were only 2-6:1 for the W251 mutants. The extra space in the acyl pocket provided by these mutants was apparently of greatest benefit for the hydrolysis of the otherwise more problematic cis isomers.

The MCE activity of the E3-251 mutants was not correlated with permethrin hydrolytic activity. Of this group of mutants, E3W251G had approximately 10-fold higher MCE activity than the remainder of the group, and yet its permethrin hydrolytic activity was among the lowest.

Combination of both the W251L and G137D mutations on to the same E3 molecule increased the activity of the enzyme for cis permethrin over wild-type levels, but decreased the activity for trans-permethrin and also malathion. However, the activity of the double mutant was not as great as that of the mutant containing the E3W251L mutation alone (i.e. the mutations did not act additively).

Some lipases are known to have a Leu residue at the position corresponding to Phe 309 in *L. cuprina* E3. The E3F309L mutant was therefore constructed with the aim of conferring activity for lipophilic substrates like pyrethroids. As can be seen from Table 2, the E3F309L mutant was much better than E3WT for both isomers. It was even more active for trans-permethrin than E3W251L, though not as active for the cis isomers. However, the MCE activity of this mutant was less than half that of the wild-type enzyme. Combination of both the F309L and W251L mutations on the same E3 molecule increased the activity for cis-permethrin and decreased the activity for trans-permethrin to E3W251L levels. In other words, the F309L mutation had very little effect on the activity of the W251L mutant for permethrin, but decreased its activity for malathion.

c) Anionic Site Mutations

Some lipases are known to have a Leu residue at the position corresponding to Phe 354 in *L. cuprina* E3. However, substitution of Phe 354 for Leu in E3 did not increase its activity for permethrin appreciably, but greatly reduced its activity for malathion. Substitution of Phe 354 for the bulkier aromatic residue, Trp, on the other hand, increased activity for both cis- and trans-permethrin 3-4-fold, but decreased MCE activity slightly. It is perhaps surprising that F354W, not F354L, should show increases in activity against the very lipophilic permethrin, given that it is a Leu that replaces Phe in some naturally occurring lipases.

Although Y148F is of little consequence for MCE activity it has large effects on permethrin kinetics and the effects are opposite in direction depending on genetic background. As a single mutant compared to wild type it shows 5-6 fold enhancement of activity for both cis and trans permethrin. As a double mutant with G137D (which as a single mutant gives values much lower than wild type), it shows a further two fold reduction for trans permethrin and and almost obliterates activity for cis permethrin. These latter results clearly imply a strong interaction of Y148 with the oxyanion hole in respect of permethrin hydrolysis.

Glu-217, the residue immediately adjacent to the catalytic serine, is thought to be important in stabilising the transition state intermediate in hydrolysis reactions. However, mutating this residue to Met (E3E217M), as found naturally in the esterase E4 of the aphid *M. persicae*, had little effect on permethrin activity but greatly reduced its MCE activity.

Example 6

Hydrolysis of Bromo-Permethrin Analogue

Table 2 also summarises the kinetic data obtained for the E3 and EST23 variants using the two cis-dibromovinyl analogues of permethrin (NRDC157). The 1S cis isomer of this dibromo analogue of permethrin was hydrolysed with similar efficiency to the 1R/1S cis permethrin by all enzymes except E3F309L and F309L/W251L. This indicates that the larger bromine atoms did not substantially obstruct access of this substrate to the catalytic centre. Although the activities with the E3WT and EST23WT enzymes were too low for significant comparison between isomers, all other enzymes except E3F309L and F309L/W251L showed 10 to 100-fold faster hydrolysis of the 1S isomer. This is the same preference for this configuration at C1 of the cyclopropane ring as found previously for 1S trans permethrin in *M. persicae* (Devonshire and Moores, 1982).

F309L showed a dramatic effect on NRDC157 kinetics. The single mutant showed little difference from wild type for 1S cis and the double with W251L showed less activity than W251L alone for this isomer. However, the 1S/1R preference was reversed, with values of 0.7:1 in the single mutant and 0.4:1 in the double. The result is the two highest values for 1R cis activities in all the data set. The value for the double mutant is in fact about 10 fold higher than those for either mutant alone.

Example 7

Hydrolysis of Type II Pyrethroids by Expressed Enzymes

Table 3 summarises the kinetic data obtained for a sub-set of the E3 and EST23 variants using the four deltamethrin cis isomers. With the exception of E3W251L and E3F309L, the 1R cis isomers of deltamethrin (whether αS or αR) were hydrolysed with similar efficiency to the 1R cis NRDC157 (which can be considered intermediate in character between permethrin and deltamethrin in that it has dibromovinyl substituent but lacks the α cyano group). Activity against 1R cis isomers was always greater with the αR than the αS conformation. E3W251L and E3F309L were markedly less efficient with the 1R cis isomers of deltamethrin than with the corresponding isomers of NRDC157.

TABLE 2

Specificity constants of natural and synthetic variants of *L. cuprina* esterase E3 and *D. melanogaster* EST23 for the cis- and trans-isomers of permethrin, malathion and the two cis-dibromovinyl analogues of permethrin (NRDC157). Ratios of the specificity constants for trans and cis permethrin, and for 1S cis and 1R cis NRDC157 are also indicated.

| | Specificity Constant ($k_{cat}/K_m$ M$^{-1}$sec$^{-1}$) | | | | |
|---|---|---|---|---|---|
| Enzyme | 1S/1R trans-permethrin | 1S/1R cis-permethrin (trans:cis ratio) | malathion | NRDC157 1S cis | NRDC157 1R cis (1S:1R ratio) |
| E3WT | 90 000 | 3 400 (27:1) | 2 600 000 | 4 700 | 630 (8:1) |
| | | Oxyanion hole mutants: | | | |
| E3G137D | 9 600 | 1 800 (5:1) | 5 100 | ND[1] | ND |
| E3G137R | 85 000 | 3 900 (22:1) | 1 200 000 | ND | ND |
| E3G137H | 26 000 | 1 600 (16:1) | 8 800 | ND | ND |
| E3G137E | 2 400 | 280 (9:1) | 19 000 | ND | ND |
| | | Acyl binding pocket mutants: | | | |
| E3W251L | 900 000 | 460 000 (2:1) | 4 800 000 | 370 000 | 5 400 (68:1) |
| E3W251S | 140 000 | 36 000 (4:1) | 6 500 000 | 35 000 | 2 900 (12:1) |
| E3W251G | 95 000 | 24 000 (4:1) | 57 000 000 | 27 000 | 1 700 (16:1) |
| E3W251T | 150 000 | 24 000 (6:1) | 4 500 000 | 24 000 | 900 (26:1) |
| E3W251A | 300 000 | 72 000 (4:1) | 5 400 000 | 67 000 | 1 200 (56:1) |
| E3F309L | 1 200 000 | 48 000 (25:1) | 1 000 000 | 5 700 | 8 000 (0.7:1) |
| E3W251L/ F309L | 810 000 | 430 000 (2:1) | 1 400 000 | 26 000 | 69 100 (0.4:1) |
| E3W251L/ G137D | 24 000 | 11 000 (2:1) | 60 000 | 12 000 | 1 100 (11:1) |
| E3P250S/ W251L | 340 000 | 110 000 (3:1) | 1 400 000 | ND | ND |

TABLE 2-continued

Specificity constants of natural and synthetic variants of L. cuprina esterase E3 and D. melanogaster EST23 for the cis- and trans-isomers of permethrin, malathion and the two cis-dibromovinyl analogues of permethrin (NRDC157). Ratios of the specificity constants for trans and cis permethrin, and for 1S cis and 1R cis NRDC157 are also indicated.

| Enzyme | Specificity Constant ($k_{cat}/K_m$ $M^{-1}sec^{-1}$) | | | | |
|---|---|---|---|---|---|
| | 1S/1R trans-permethrin | 1S/1R cis-permethrin (trans:cis ratio) | malathion | NRDC157 1S cis | NRDC157 1R cis (1S:1R ratio) |
| Anionic site mutants: | | | | | |
| E3Y148F | 580 000 | 17 000 (34:1) | 3 100 000 | ND | ND |
| E3Y148F/G137D | 4 100 | 47 (87:1) | 12 000 | ND | ND |
| E3E217M | 93 000 | 4 400 (21:1) | 77 000 | ND | ND |
| E3F354W | 350 000 | 8 800 (40:1) | 1 600 000 | ND | ND |
| E3F354L | 104 400 | 2 700 (38:1) | 106 000 | ND | ND |
| EST23 enzymes: | | | | | |
| EST23WT | 21 000 | 890 (24:1) | 2 700 000 | 990 | 330 (3:1) |
| EST23W251L | 260 000 | 160 000 (2:1) | 2 300 000 | 72 000 | 1 200 (60:1) |
| EST23G137D | 2 500 | —[2] | — | ND | ND |

[1]Not determined
[2]Not substantially different from values obtained using control cell extracts Significantly, the 251 mutant with the highest deltamethrin activities was W251S, while W251L (highest for the other two pyrethroids), and W251G (highest for malathion) gave the lowest deltamethrin activities of the five 251 mutants. This suggests that accommodation of the αcyano moiety of the leaving group may be the major impediment to efficient deltamethrin hydrolysis, sufficient to prevent any significant hydrolysis by wild type E3. Accommodation of substrate requires significantly different utilisation of space across the active site compared to other substrates, such that substitution of W251 in the acyl pocket with a smaller residue allows useful accommodation, particularly for αR isomers. Importantly, however, the details of the spatial requirements, and therefore the most efficacious mutants, differ from those for the other pyrethroids.

The activity of all enzymes with the 1S cis isomers of deltamethrin was dramatically less than with the corresponding isomer of NRCC157 lacking the α cyano group. This dramatic influence of the α cyano group appears to be expressed with this 1S conformation at C1 of the cyclopropane group. With the exception of some of the least active mutants, activity against 1S cis isomers was again always greater with the αR than the αS conformation.

Example 8

General Discussion

Together, the permethrin and NRDC157 results for the 251 series mutants generate some quite strong and simple inferences about acyl binding constraints in E3/EST23. Overall, as with malathion, 251 replacements that should generate a more spacious acyl pocket do facilitate the accommodation/stabilisation of the bulky acyl groups of these substrates. These replacements are beneficial to the hydrolysis of all the isomers

TABLE 3

Specificity constants for the four deltamethrin cis isomers

| Enzyme | Specificity Constant ($k_{cat}/K_m$ $M^{-1}sec^{-1}$) | | | |
|---|---|---|---|---|
| | 1S cis αR deltamethrin | 1S cis αS deltamethrin | 1R cis αR deltamethrin | 1R cis αS deltamethrin |
| E3WT | —[1] | — | — | — |
| E3G137D | — | — | 890 | 560 |
| E3G137R | — | — | 670 | 350 |
| E3G137H | ND | ND | ND | ND |
| E3G137E | ND | ND | ND | ND |
| E3W251L | 990 | 880 | 380 | — |
| E3W251S | 4 600 | 2 460 | ND[2] | ND |
| E3W251G | 700 | 170 | 690 | 350 |
| E3W251T | 2 900 | 520 | 2 100 | 1 300 |
| E3W251A | 2 000 | 660 | 1 300 | 730 |
| E3F309L | 2 400 | 810 | 1 600 | 840 |
| E3W251L/G137D | 3 600 | 410 | 2 700 | 1 100 |
| Est23WT | 450 | 750 | — | — |
| Est23W251L | 980 | 550 | 1000 | 430 |

[1]Not substantially different from values obtained using control cell extracts
[2]Not determined generated by the two stereocentres across the cyclopropane ring. While the trans isomers are strongly preferred by wild type enzyme, the mutants can also hydrolyse at least part of the cis isomer mix relatively well. However, within the cis isomers the improvements in the mutants is much more marked for the 1S cis isomers. The 1R cis isomers, which are the most problematic of all configurations for wild type enzyme, remain the most problematic for the mutants. Within the mutant series, the improved kinetics are not simply explained by the reduction in side chain size; the smallest substitution does not give the highest activities, as it does for malathion. Indeed the best kinetics are obtained with W251L, although Leu has the greatest side chain size of all the replacements tested.

In contrast to the relatively simple and consistent patterns seen for permethrin and NRDC157, the deltamethrin results for the 251 series mutants are quite complex and difficult to interpret. As might be expected from their enhanced kinetics for the other substrates, they do show overall better activities than wild type for the four cis deltamethrin isomers, albeit as with wild type they are much lower in absolute terms than for the other substrates. However, the preference for 1S over 1R isomers, which is so strong in respect of NRDC157, is weak at best in the deltamethrin data. On the other hand there is a clear trend across all the mutants for a preference for the αR over αS isomers. It is generally only of the order of 2:1, but notably it is opposite to the trend shown by wild type EST23. It is at first sight unexpected that these presumptive acyl binding pocket replacements should affect αR/αS stereopreferences because the latter apply to the α-cynano moiety in the (alcohol) leaving group of the substrate.

Overall the F309L data clearly show a major effect of this residue on the kinetics of pyrethroid hydrolysis. At one level there are parallels with the results for the W251 series mutants, both data sets showing enhanced kinetics consistent with expectations based on the provision of greater space in the acyl binding pocket. However, there are also important differences, with the W251 series disproportionately active for the cis vs trans isomers of permethrin and F309L disproportionately active with 1R vs 1S isomers of cis NRDC157. The replacements at the two sites also show strong interactions, consistent with them contributing to a shared structure and function in the acyl binding pocket. For example, both the disproportionate enhancement of the W251 mutants for cis permethrin and the disproportionate enhancement of F309L for 1R cis NRDC157 behave as dominant characters in the double mutant. The 251 and 309 mutants have quantitatively similar enhancing effects on activities and the same stereospecificities in respect of deltamethrin hydrolysis and the stereospecific differences seen with the smaller pyrethroids are not seen. However, we argue that the additional bulk of the αcyano moiety in its leaving group requires such a radical reallocation of space across the active site that the stereospecificities evident with the smaller pyrethroids are overridden.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Broomfield, C. A. (1999). *Chemico-Biological Interactions* 120: 251-256.

Campbell, P. M., Harcourt, R. L., Crone, E. J., Claudianos, C., Hammock, B. D., Russell, R. J. and Oakeshott, J. G. (2001) *Insect Biochem Molec Biol* 31:513-520.

Campbell, P. M., Newcomb, R. D., Russell, R. J. and Oakeshott, J. G. (1998a) *Insect Biochem Molec Biol* 28, 139-150.

Campbell, P. M., Yen, J. L., Masoumi, A., Russell, R. J., Batterham, P., McKenzie, J. A., and Oakeshott, J. G. (1998b) *J. Econ. Entomol.* 91:367-375.

Claudianos, C., Crone, E., Coppin, C., Russell, R. and Oakeshott, J. (2002) In: Marshall Clark, J. and Yamagushi, I., (Eds.) *Agrochemical Resistance: Extent, Mechanism and Detection.* (in press)

Claudianos, C., Russell, R. J. and Oakeshott, J. G. (1999) *Insect Biochem Molec Biol* 29, 675-86.

Cygler, M. and Schrag, J. D. (1997) *Methods Enzymol* 284, 3-27.

Derewenda, U., Brzozwski, A. M., Lawson, D. M., Derewenda, Z. S. (1992) *Biochemistry* 31:1532-1541.

Devonshire, A. L., Heidari, R., Bell, K. L., Campbell, P. M., Campbell, B. E., Odgers, W. A., Oakeshott, J. G. and Russell, R. J. Kinetic Efficiency of Mutant Carboxylesterases Implicated in Organophosphate Insecticide Resistance. (in preparation)

Devonshire, A. L. and Moores, G. D. (1982) *Pestic. Biochem. Physiol.* 18, 235-246.

Fournier, D., Bride, J.-M., Hoffmann, F. and Karch, F. (1992) *J. Biol. Chem.* 267, 14270-14274.

Gordon, R. K., Feaster, S. R., Russell, A. J., Lejeune, K. E., Maxwell, M. D., Lenz, D. E., Ross, M. and Doctor, B. P. (1999) *Chem Biol Interact* 14, 463-70.

Grochulski, P., Li, Y., Schrag, J. D., Bouthillier, F., Smith, P., Harrison, D., Rubin, B., Cygler, M. (1993). *J Biol Chem* 268, 12843-12847.

Harel, M., Kryger, G., Rosenberry, T. L., Mallender, W. D., Lewis, T., Fletcher, R. J., Guss, M., Silman, I. and Sussman, J. L. (2000) *Protein Science* 9, 1063-1072.

Järv, J. (1984) *Bioorganic Chemistry* 12, 259-278.

Koellner, G., Kryger, G., Millard, C. B., Silman, I., Sussman, J. L. and Steiner, T. (2000) *The Journal of Molecular Biology* 296, 713-735.

Lejeune, K. E., Wild, J. R. and Russell, A. J. (1998) *Nature* 395, 27-8.

Martinez, C., Nicolas, A., van Tilbeurgh, H., Egloff, M. P., Cudrey, C., Verger, R. and Cambillau, C. (1994) *Biochemistry* 33, 83-9.

Myers, M. A., Healy, M. J. and Oakeshott, J. G. (1993) *Biochem Genet* 31, 259-78.

Nair, H. K., Seravalli, J., Arbuckle, T. and Quinn, D. M. (1994) *Biochemistry* 33, 8566-76.

Needleman, S. B. and Wunsch, C. D. (1970) *J Mol Biol* 48, 443-53.

Newcomb, R. D., Campbell, P. M., Ollis, D. L., Cheah, E., Russell, R. J. and Oakeshott, J. G. (1997) *Proc Natl Acad Sci USA* 94, 7464-8.

Oakeshott, J. G., Claudianos, C., Russell, R. J. and Robin, G. C. (1999) *BioEssays* 21, 1031-42.

Oakeshott, J. G., van Papenrecht, E. A., Boyce, T. M., Healy, M. J. and Russell, R. J. (1993) *Genetica* 90, 239-268.

Ordentlich, A., Barak, D., Kronman, C., Ariel, N., Segal, Y., Velan, B, and Shaferman, A. (1998) *The Journal of Biological Chemistry* 273, 19509-19517.

Ordentlich, A., Barak, D., Kronman, C., Ariel, N., Segal, Y., Velan, B. and Shaferman, A. (1996) *The Journal of Biological Chemistry* 271, 11953-11962.

Ordentlich, A., Barak, D., Kronman, C., Ariel, N., Segal, Y., Velan, B. and Shaferman, A. (1995) *The Journal of Biological Chemistry* 270, 2082-2091.

Ordentlich, A., Barak, D., Kronman, C., Flashner, Y., Leitner, M., Segal, Y., Ariel, N., Cohen, S., Velan, B. and Shafferman, A. (1993) *The Journal of Biological Chemistry* 268, 17083-17095.

Patten, P. A., Howard, R. J. and Stemmer, W. P. (1997) *Curr Opin Biotechnol* 8, 724-33.

Petrikovics, I., Cheng, T. C., Papahadjopoulos, D., Hong, K., Yin, R., DeFrank, J. J., Jaing, J., Zong, Z. H., McGuinn, W. D., Sylvester, D., Pei, L., Madec, J., Tamulinas, C., Jaszberenyi, J. C., Barcza, T. and Way, J. L. (2000a) *Toxicol Sci* 57, 16-21.

Petrikovics, I., McGuinn, W. D., Sylvester, D., Yuzapavik, P., Jaing, J., Way, J. L., Papahadjopoulos, D., Hong, K., Yin, R., Cheng, T. C., and DeFrank, J. J. (2000b) *Drug Delivery* 7: 83-89.

Qian, N. and Kovach, I. M. (1993) *FEBS Lett* 336, 263-6.

Robin, C., R. J. Russell, K. M. Medveczky, and J. G. Oakeshott. (1996) *J Mol Evol* 43:241-52.

Shafferman, A., Velan, B., Orentlich, A., Kronman, C., Grosfeld, H., Leitner, M., Flachner, Y., Cohen, S., Barak, D. and Ariel, N. (1992) *EMBO J.* 11, 3561-3568.

Stryer, L. (1981) Biochemistry. p 115, W. H. Freeman, San Francisco.

Sussman, J. S., Harel, M., Frolov, F., Oefner, C., Goldman, A., Toker, L. and Silman, I. (1991) *Science* 253, 872-879.

Thomas, B. A., Church, W. B., Lane, T. R. and Hammock, B. D. (1999) *Proteins* 34,184-96.

Villatte, F., Ziliani, P., Marcel, V., Menozzi, P. and Fournier, D. (2000) *Pesticide Biochemistry and Physiology* 95-102.

Walsh, S. B., Dolden, T. A., Moores, G. D., Kristensen, M., Lewis, T., Devonshire, A. L. and Williamson, M. S. (2001) *Biochem J* 359, 175-81.

Yao, H., Chunling, Q., Williamson, M. S. and Devonshire, A. L. (1997) *Clin. J. Biotechnol.* 13: 177-183.

Zhu, Y.-C., Dowdy, A. K. and Baker, J. E. (1999) *Insect Biochem Molec. Biol.* 29:417-425.

---

The invention claimed is:

1. A purified polypeptide which is a mutant of a Dipteran esterase, wherein the polypeptide comprises a leucine, alanine or valine at residue number 309 of SEQ ID NO: 1, wherein the mutant Dipteran esterase hydrolyzes a hydrophobic ester pesticide or toxin, and wherein the mutant comprises amino acid sequence which is at least 95% identical to SEQ ID NO: 1.

2. A fusion polypeptide comprising the polypeptide according to claim 1 fused to at least one other polypeptide sequence.

3. An isolated polynucleotide encoding the polypeptide according to claim 1.

4. A vector for replication and/or expression the isolated polynucleotide according to claim 3.

5. An isolated host cell transformed or transfected with the vector of claim 4.

6. A composition for hydrolysing a hydrophobic ester pesticide or toxin, the composition comprising the polypeptide according to claim 1, and one or more acceptable carriers.

7. The polypeptide of claim 1 which is at least 97% identical to SEQ ID NO:1.

8. The polypeptide of claim 1, wherein the hydrophobic ester pesticide or toxin is a pyrethroid.

9. The polypeptide of claim 8, wherein the pyrethroid is a Type I pyrethroid.

10. The polypeptide of claim 9, wherein the Type I pyrethroid is selected from the group consisting of: 1S/1R trans permethrin, 1S/1R cis permethrin, NRDC157 1S cis, and NRDC157 1R cis.

11. The polypeptide of claim 8, wherein the pyrethroid is deltamethrin.

12. A purified polypeptide that hydrolyzes a hydrophobic ester pesticide or toxin, which polypeptide comprises an amino acid sequence which is at least 95% identical to SEQ ID NO: 1, wherein the polypeptide does not comprise a phenylalanine at residue number 309 of SEQ ID NO: 1, and the polypeptide has greater space in the acyl binding pocket than a polypeptide which comprises an amino acid sequence which is at least 95% identical to SEQ ID NO: 1 and which comprises a phenylalanine at residue number 309 of SEQ ID NO: 1.

13. The polypeptide of claim 12 which comprises a leucine at residue number 309 of SEQ ID NO: 1.

14. The polypeptide of claim 12 which comprises a leucine at residue number 251 of SEQ ID NO: 1.

15. The polypeptide of claim 1 which has an enhanced ability to hydrolyse 1S/1R trans permethrin and/or 1S/1R cis permethrin when compared to a polypeptide which comprises an amino acid sequence which is at least 95% identical to SEQ ID NO:1 and which comprises a phenylalanine residue at a position corresponding to residue number 309 of SEQ ID NO:1.

16. A purified polypeptide that hydrolyzes a hydrophobic ester pesticide or toxin, which polypeptide comprises an amino acid sequence whish is at least 95% identical to SEQ ID NO: 1, wherein the polypeptide does not comprise a phenylalanine at residue number 309 of SEQ ID NO: 1, and the polypeptide has greater space in the acyl binding pocket than a polypeptide which comprises the amino acid sequence set forth in SEQ ID NO: 1.

17. A fusion polypeptide comprising a polypeptide according to claim 12 fused to at least one other polypeptide sequence.

18. An isolated polynucleotide encoding the polypeptide according to claim 12.

19. A vector for expression comprising a polynucleotide encoding the polypeptide of claim 12.

20. An isolated host cell transformed or transfected with the vector of claim 19.

21. A composition for hydrolyzing a hydrophobic ester pesticide or toxin, the composition comprising the polypeptide according to claim 12, and one or more acceptable carriers.

22. A fusion polypeptide comprising the polypeptide according to claim 16 fused to at least one other polypeptide sequence.

23. An isolated polynucleotide encoding the polypeptide of claim 16.

24. A vector for replication and/or expression comprising the polynucleotide of claim 23.

25. An isolated host cell transformed or transfected with the vector of claim 24.

26. A composition for hydrolyzing a hydrophobic ester pesticide or toxin, the composition comprising the polypeptide of claim 16, and one or more acceptable carriers.

* * * * *